(12) United States Patent
Barske et al.

(10) Patent No.: US 8,758,754 B2
(45) Date of Patent: Jun. 24, 2014

(54) NOGO-A BINDING MOLECULES AND PHARMACEUTICAL USE THEREOF

(75) Inventors: Carmen Barske, Loerrach (DE); Stefan Frentzel, Lörrach (DE); Anis Khurso Mir, Bartenheim (FR); Martin E. Schwab, Zürich (CH); Alessandra Vitaliti Garami, Oberwill (CH)

(73) Assignee: Novartis AG, Basel (CH)

( * ) Notice: Subject to any disclaimer, the term of this patent is extended or adjusted under 35 U.S.C. 154(b) by 314 days.

(21) Appl. No.: 13/422,642

(22) Filed: Mar. 16, 2012

(65) Prior Publication Data
US 2012/0171215 A1    Jul. 5, 2012

Related U.S. Application Data

(63) Continuation of application No. 12/740,777, filed as application No. PCT/EP2008/064501 on Oct. 27, 2008, now Pat. No. 8,163,285.

(60) Provisional application No. 61/001,741, filed on Nov. 2, 2007.

(30) Foreign Application Priority Data

Nov. 2, 2007    (EP) .................................... 07119847

(51) Int. Cl.
*A61K 39/395*    (2006.01)
(52) U.S. Cl.
USPC ...................................................... 424/139.1
(58) Field of Classification Search
CPC . A61K 2039/505; A61K 38/00; C07K 16/18; C07K 2317/55; C07K 2317/56; C07K 2317/565; C07K 2316/96; C07K 16/22; C07K 2317/21; C07K 16/28; C07K 2317/76
USPC .......... 424/139.1, 130.1, 133.1, 172.1, 93.21, 424/141.1, 143.1, 152.1, 185.1; 435/331; 514/1.1, 17.7; 530/387.9, 387.1, 389.1, 530/388.1
See application file for complete search history.

(56) References Cited

U.S. PATENT DOCUMENTS

| 2005/0142140 A1 | 6/2005 | Massberg et al. |
| 2007/0141054 A1 | 6/2007 | Kataoka et al. |
| 2008/0044411 A1 | 2/2008 | O'neil et al. |

FOREIGN PATENT DOCUMENTS

| WO | 2004/052932 A | 6/2004 |
| WO | 2005/028508 A | 3/2005 |
| WO | 2005/061544 A | 7/2005 |
| WO | 2007/003421 A | 1/2007 |
| WO | 2007/068750 A | 6/2007 |
| WO | WO2009056631 | 5/2009 |
| WO | WO 2009/106356 A1 | 9/2009 |
| WO | WO 2010/044506 A2 | 4/2010 |

OTHER PUBLICATIONS

Onose et al. A review of published reports on neuroprotection in spinal cord injury. Spinal Cord. Oct. 2009;47(10):716-26. Epub Jul. 14, 2009.*
Weissner et al. Anti-Nogo-A antibody infusion 24 hours after experimental stroke improved behavioral outcome and corticospinal plasticity in normotensive and spontaneously hypertensive rats. J Cereb Blood Flow Metab. Feb. 2003;23(2):154-65.*
Zhu et al. Increased expression of the Nogo receptor in the hippocampus and its relation to the neuropathology in Alzheimer's disease. Hum Pathol. Mar. 2007;38(3):426-34. Epub Dec. 22, 2006.*
Inoue et al. Inhibition of the leucine-rich repeat protein LINGO-1 enhances survival, structure, and function of dopaminergic neurons in Parkinson's disease models. Proc Natl Acad Sci U S A. Sep. 4, 2007;104(36):14430-5. Epub Aug. 28, 2007.*
Teng et al. Nogo-A and Nogo-66 receptor in amyotrophic lateral sclerosis. J Cell Mol Med. Aug. 2008;12(4):1199-204. Epub Apr. 15, 2008.*
Freund Patrick et al: "Anti-Nogo-A antibody treatment enhances sprouting of corticospinal axons rostral to a unilateral cervical spinal cord lesion in adult macaque monkey," The Journal of Comparative Neurology, vol . 502, No. 4, Jun. 1, 2001, pp. 644-659.
Grainger D W: "Controlled-release and local delivery of therapeutic antibodies", Expert Opinion on Biological Therapy, Ashley, London, GB, vol. 4, No. 7, 2004, pp. 1029-1044.
Hunt D et al: "The Nogo receptor, its ligands and axonal regeneration in the spinal cord; a review", Journal of Neurocytology, Chapman and Hall, GB, vol . 31, No. 2, Feb. 2002, pp. 93-120.
Liebscher Thomas et al: "Nogo-A antibody improves regeneration and locomotion of spinal cord-Injured rats", Annals of Neurology, vol. 58, No. 5, Nov. 2005, pp. 706-719.
Shih-Yen Tsai et al: "Intrathecal treatment with anti-Nogo-A antibody improves functional recovery in adult rats after stroke", Experimental Brain Research, Springer-Verlag, BE, vol. 182, No. 2, Aug. 24, 2007, pp. 261-266.
Weinmann et al: "Intrathecally infused antibodies against Nogo-A penetrate the CNS and downregulate the endogenous neurite growth inhibitor Nogo-A", Molecular and Cellular Neurosciences, San Diego, US, vol. 32, No. 1-2, May 2006, pp. 161-173.
Wiessner C et al: "Anti-Nogo-A Antibody Infusion 24 Hours After Experimental Stroke improved Behavioral Outcome and Corticospinal Plasticity in Normotensive and Spontaneously Hypertensive Rats", Journal of Cerebral Blood Flow and Metabolism, Raven Press, Ltd., New York, NY, US, vol . 23, No. 2, Feb. 2003, pp. 154-165.

(Continued)

*Primary Examiner* — Gregory S Emch
(74) *Attorney, Agent, or Firm* — Karen A. Lacourse

(57) ABSTRACT

The present invention provides a binding molecule which is capable of binding to the human NogoA polypeptide or human NiG with a dissociation constant <1000 nM, a polynucleotide encoding such binding molecule; an expression vector comprising said polynucleotide; an expression system comprising a polynucleotide capable of producing a binding molecule; an isolated host cell which comprises an expression system as defined above; the use of such binding molecule as a pharmaceutical, especially in the treatment of a disease of the peripheral (PNS) and/or central (CNS) nervous system; a pharmaceutical composition comprising said binding molecule; and a method of treatment of a disease of the peripheral (PNS) and/or central (CNS) nervous system.

3 Claims, 11 Drawing Sheets

(56) References Cited

OTHER PUBLICATIONS

Holt Lucy J. et al., "Domain antibodies: proteins for therapy", Trends in Biotechnology; vol. 21, No. 11, pp. 484-490, issn 0167-7799, Nov. 2003.

Davies Julian et al., "Affinity improvement of single antibody VH domains: residues in all three hypervariable regions affect antigen biding", ELSEVIER, Immunotechnology, XP004070292; issn 1380-2933; vol. 2, No. 3, p. 169-179, Sep. 1996.

Maynard Jennifer; Georgiou G., "Antibody Engineering", annual review biochemistry; pp. 339-376, 2000.

Pini Alessandro et al., "Design and Use of a Phage Display Library", The Journal of Biological Chemistry, vol. 273, No. 34, pp. 21769-21776, Aug. 21, 2998.

Rudikoff Stuart et al., "Single amino acid substitution altering antigen-biding specificity", Proc. Natl. Acad. Sci. USA; vol. 79, pp. 1979-1983, Mar. 1982.

Vajdos Felix F. et al., "Comprehensive functional maps of the antigen-biding site of an anti-ErbB2 antibody obtained with shotgun scanning mutagenesis", J. Mol. Biol.; 320(2); pp. 415-428, Jul. 5, 2002.

Zander Hilke et al., "Epitope mapping of the neuronal growth inhibitor Nogo-A for the Nogo receptor and the cognate monoclonal antibody IN-1 by means of the SPOT technique", Journal molecular recognition, 20(3); p. 185-196, May-Jun. 2007.

Oertle Thomas et al., "Nogo-A Inhibits Neurite Outgrowth and Cell Spreading with Three Discrete Regions", The Journal of Neuroscience; 23(13); p. 5393-5406, Jul. 2, 2003.

Biological methods of cancer treatment, Ed. Devita V.T. Hellman S., Rosenberg S.A., Moscow, publ. Meditsina 2002, p. 538, 2002.

Chalimskaya L.M., "Chemical synthesis of proteins and nucleic acids by using automated synthesizers", Sorovskli obrazovateinyl zhumal, vol. 6, No. 10, pp. 37-42, 2000.

Brosamle et al., "Regeneration of Lesioned Corticospinal Tract Fibers in the Adult Rat Induced by a Recombinant, Humanized IN-1 Antibody Fragment", J. Neurosci., 20(21):8061-8068, Nov. 1, 2000.

Freund et al., "Nogo-A-Specific antibody treatment enhances sprouting and functional recovery after cervical lesion in adult primates", Nat. Med., vol. 12, No. 7, pp. 790-792, Jul. 2006.

Wu et al., "Humanization of a Murine Monoclonal Antibody by Simultaneous Optimization of Framework and CDR Residues", J. Mol. Biol. vol. 294, pp. 151-162, (1999).

Ohno et al., "Antigen-binding specificities of antibodies are primarily determined by seven residues of VH", Proc. Natl. Acad. Sci. USA, vol. 82, pp. 2945-2949, May 1985.

Zhang et al., "Mediated efflux of IgG molecules from brain to blood-brain barrier", Journal of Neuroimmunology, vol. 114, pp. 168-172, 2001.

* cited by examiner

Figure 1

```
ATG GAA GCC CCA GCT CAG CTT CTC TTC CTC CTG CTA CTC TGG CTC CCA GAT ACC ACC GGA
 M   E   A   P   A   Q   L   L   F   L   L   L   W   L   P   D   T   T   G

GAA ATT GTG TTG ACA CAG TCT CCA GCC ACC CTG TCT TTG TCT CCA GGG GAA AGA GCC ACC
 E   I   V   L   T   Q   S   P   A   T   L   S   L   S   P   G   E   R   A   T

CTC TCC TGC AGG GCC AGT CAG AGT GTT AGC AGC TAC TTA GCC TGG TAC CAA CAG AAA CCT
 L   S   C   R   A   S   Q   S   V   S   S   Y   L   A   W   Y   Q   Q   K   P

GGC CAG GCT CCC AGG CTC CTC ATC TAT GAT GCA TCC AAC AGG GCC ACT GGC ATC CCA GCC
 G   Q   A   P   R   L   L   I   Y   D   A   S   N   R   A   T   G   I   P   A

AGG TTC AGT GGC AGT GGG TCT GGG ACA GAC TTC ACT CTC ACC ATC AGC AGC CTA GAG CCT
 R   F   S   G   S   G   S   G   T   D   F   T   L   T   I   S   S   L   E   P

GAA GAT TTT GCA GTT TAT TAC TGT CAG CAG CGT AGC AAC TGG CCG ATC ACC TTC GGC CAA
 E   D   F   A   V   Y   Y   C   Q   Q   R   S   N   W   P   I   T   F   G   Q

GGG ACA CGA CTG GAG ATT AAA CGA ACT GTG GCT GCA CCA TCT GTC TTC ATC TTC CCG CCA
 G   T   R   L   E   I   K   R   T   V   A   A   P   S   V   F   I   F   P   P

TCT GAT GAG CAG TTG AAA TCT GGA ACT GCC TCT GTT GTG TGC CTG CTG AAT AAC TTC TAT
 S   D   E   Q   L   K   S   G   T   A   S   V   V   C   L   L   N   N   F   Y

CCC AGA GAG GCC AAA GTA CAG TGG AAG GTG GAT AAC GCC CTC CAA TCG GGT AAC TCC CAG
 P   R   E   A   K   V   Q   W   K   V   D   N   A   L   Q   S   G   N   S   Q

GAG AGT GTC ACA GAG CAG GAC AGC AAG GAC AGC ACC TAC AGC CTC AGC AGC ACC CTG ACG
 E   S   V   T   E   Q   D   S   K   D   S   T   Y   S   L   S   S   T   L   T

CTG AGC AAA GCA GAC TAC GAG AAA CAC AAA GTC TAC GCC TGC GAA GTC ACC CAT CAG GGC
 L   S   K   A   D   Y   E   K   H   K   V   Y   A   C   E   V   T   H   Q   G

CTG AGC TCG CCC GTC ACA AAG AGC TTC AAC AGG GGA GAG TGT TAG
 L   S   S   P   V   T   K   S   F   N   R   G   E   C
```

Figure 2

```
ATG GAG TTT GGG CTG AGC TGG GTT TTC CTT GTT GCT ATT TTA GAA GGT GTC CAG TGT GAG
 M   E   F   G   L   S   W   V   F   L   V   A   I   L   E   G   V   Q   C   E

GTG CAG CTG GTG GAG TCT GGG GGA GGC TTG GTC CAG CCT GGG GGG TCC CTG AGA CTC TCC
 V   Q   L   V   E   S   G   G   G   L   V   Q   P   G   G   S   L   R   L   S

TGT GCA GCT TCT GGA TTC ACC TTT AGT AAC TAT TGG ATG AGC TGG GTC CGC CAG GCT CCG
 C   A   A   S   G   F   T   F   S   N   Y   W   M   S   W   V   R   Q   A   P

GGG AAA GGG CTG GAG TGG GTG GCC ACC ATA AAG CAA GAT GGA AGT CAG AAA AAC TAT GTG
 G   K   G   L   E   W   V   A   T   I   K   Q   D   G   S   Q   K   N   Y   V

GAC TCT GTG AAG GGC CGA TTC ACC ATC TCC AGA GAC AAC GCC AAG AAC TCA CTG TAT CTG
 D   S   V   K   G   R   F   T   I   S   R   D   N   A   K   N   S   L   Y   L

CGA TTG AAC AGC CTG AGA GCC GAG GAC ACG GCT GTG TAT TAC TGT GCG ACT GAA CTC TTC
 R   L   N   S   L   R   A   E   D   T   A   V   Y   Y   C   A   T   E   L   F

GAT CTC TGG GGC CGT GGC TCC CTG GTC ACC GTC TCC TCA GCC TCC ACC AAG GGC CCA TCG
 D   L   W   G   R   G   S   L   V   T   V   S   S   A   S   T   K   G   P   S

GTC TTC CCC CTG GCA CCC TCC TCC AAG AGC ACC TCT GGG GGC ACA GCG GCC CTG GGC TGC
 V   F   P   L   A   P   S   S   K   S   T   S   G   G   T   A   A   L   G   C

CTG GTC AAG GAC TAC TTC CCC GAA CCG GTG ACG GTG TCG TGG AAC TCA GGC GCC CTG ACC
 L   V   K   D   Y   F   P   E   P   V   T   V   S   W   N   S   G   A   L   T

AGC GGC GTG CAC ACC TTC CCG GCT GTC CTA CAG TCC TCA GGA CTC TAC TCC CTC AGC AGC
 S   G   V   H   T   F   P   A   V   L   Q   S   S   G   L   Y   S   L   S   S

GTG GTG ACC GTG CCC TCC AGC AGC TTG GGC ACC CAG ACC TAC ATC TGC AAC GTG AAT CAC
 V   V   T   V   P   S   S   S   L   G   T   Q   T   Y   I   C   N   V   N   H

AAG CCC AGC AAC ACC AAG GTG GAC AAG AGA GTT GAG CCC AAA TCT TGT GAC AAA ACT CAC
 K   P   S   N   T   K   V   D   K   R   V   E   P   K   S   C   D   K   T   H

ACA TGC CCA CCG TGC CCA TAA
 T   C   P   P   C   P
```

Figure 3

DNA sequence light chain variable part:

gaaattgtgttgacacagtctccagccaccctgtctttgtctccaggggaaagagccaccctctcctgcagggcc
agtcagagtgttagcagctacttagcctggtaccaacagaaacctggccaggctcccaggctcctcatctatgat
gcatccaacagggccactggcatcccagccaggttcagtggcagtgggtctgggacagacttcactctcaccat
cagcagcctagagcctgaagattttgcagtttattactgtcagcagcgtagcaactggccgatcaccttcggcca
agggacaaagcttgaaatcaaa

DNA sequence heavy chain variable part:

gaggtgcagctggtggagtctggggggaggcttggtccagcctggggggtccctgagactctcctgtgcagcttct
ggattcacctttagtaactattggatgagctgggtccgccaggctccggggaaagggctggagtgggtggccac
cataaagcaagatggaagtcagaaaaactatgtggactctgtgaagggccgattcaccatctccagagacaa
cgccaagaactcactgtatctgcgattgaacagcctgagagccgaggacacggctgtgtattactgtgcgactg
aactcttcgatctctggggccgtggctccctggtcaccgtctcctca

Figure 4

6A3 IgG4 light chain variable and constant part, including leader sequence:

*LEADER*                                                                                    *CDRL-1*
*MSVLTQVLALLLLWLTGTRC*EIVLTQSPATLSLPGERATLSCRASQSVSSYLA
WY
                 *CDRL-2*
      *CDRL-3*
QQKPGQAPRLLIYDASNRATGIPARFSGSGSGTDFTLTISSLEPEDFAVYYCQQ
RSN
               Cκ
WPITFGQGTKLEIKRTVAAPSVFIFPPSDEQLKSGTASVVCLLNNFYPREAKVQ
WKVDNALQSGNSQESVTEQDSKDSTYSLSSTLTLSKADYEKHKVYACEVTHQ
GLSSPVTKSFNRGEC

6A3 IgG4 heavy chain complete aa-sequence including leader, CH1, hinge region, CH2 and CH3:

*LEADER*
*CDR-H1*
*MAWVWTLPFLMAAAQSVQA*EVQLVESGGGLVQPGGSLRLSCAASGFTFSNY
WM
                        *CDR-H2*
SWVRQAPGKGLEWVATIKQDGSQKNYVDSVKGRFTISRDNAKNSLYLRLNSLR
AE         *CDR-H3*
DTAVYYCATELFDLWGRGSLVTVSS
*CH1*
ASTKGPSVFPLAPCSRSTSESTAALGCLVKDYFPEPVTVSWNSGALTSGVHTF
PAV                                                            *HINGE*
LQSSGLYSLSSVVTVPSSSLGTKTYTCNVDHKPSNTKVDKRV
ESKYGPPCPSCP
*CH2*
APEFLGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIEKTIS
KAK
*CH3*
GQPREPQVYTLPPSQEEMTKNQVSLTCLVKGFYPSDIAVEWESNGQPENNYK
TTPPVLDSDGSFFLYSRLTVDKSRWQEGNVFSCSVMHEALHNHYTQKSLSLSL
GK

Figure 5

6A3 IgG1 light chain with CDRs:

```
        Leader
M E A P A Q L L F L L L L W L P D T T G

E I V L T Q S P A T L S L S P G E R A T
             CDR-L1
L S C R A S Q S V S S Y L A W Y Q Q K P
                        CDR-L2
G Q A P R L L I Y D A S N R A T G I P A

R F S G S G S G T D F T L T I S S L E P
                     CDR-L3
E D F A V Y Y C Q Q R S N W P I T F G Q

G T R L E I K R T V A A P S V F I F P P

S D E Q L K S G T A S V V C L L N N F Y

P R E A K V Q W K V D N A L Q S G N S Q

E S V T E Q D S K D S T Y S L S S T L T

L S K A D Y E K H K V Y A C E V T H Q G

L S S P V T K S F N R G E C
```

6A3 IgG1 heavy chain with CDRs:

```
        Leader
M E F G L S W V F L V A I L E G V Q C E

V Q L V E S G G G L V Q P G G S L R L S
             CDR-H1
C A A S G F T F S N Y W M S W V R Q A P
                         CDR-H2
G K G L E W V A T I K Q D G S Q K N Y V

D S V K G R F T I S R D N A K N S L Y L
                                CDR-H3
R L N S L R A E D T A V Y Y C A T E L F

D L W G R G S L V T V S S A S T K G P S

V F P L A P S S K S T S G G T A A L G C

L V K D Y F P E P V T V S W N S G A L T

S G V H T F P A V L Q S S G L Y S L S S

V V T V P S S S L G T Q T Y I C N V N H

K P S N T K V D K R V E P K S C D K T H

T C P P C P
```

Figure 8
Figure 8a:
MO3.13 cells
5mM 6A3 IgG4
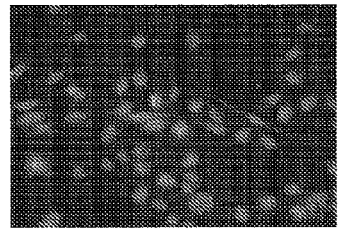 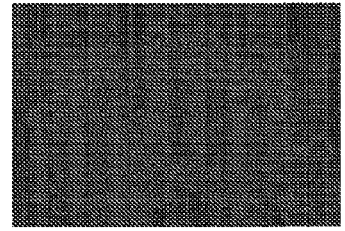
Secondary Antibody only
Figure 8b:
HOG cells
5mM 6A3 IgG4
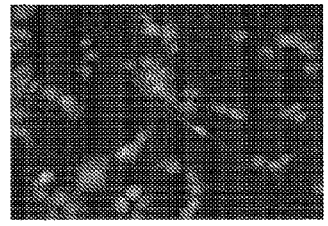 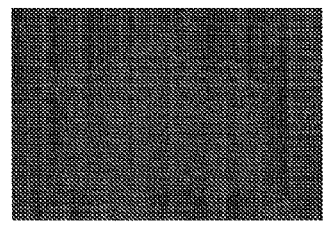
Secondary Antibody only Cohort=3 (15 mg/day for 14 days)

SEQUENCE LISTING

```
<160> NUMBER OF SEQ ID NOS: 33

<210> SEQ ID NO 1
<211> LENGTH: 3919
<212> TYPE: DNA
<213> ORGANISM: Homo sapiens
<220> FEATURE:
<221> NAME/KEY: CDS
<222> LOCATION: (1)..(3579)
<223> OTHER INFORMATION: Human NogoA

<400> SEQUENCE: 1 atg gaa gac ctg gac cag tct cct ctg gtc tcg tcc tcg gac agc cca      48
Met Glu Asp Leu Asp Gln Ser Pro Leu Val Ser Ser Ser Asp Ser Pro
1               5                   10                  15 ccc cgg ccg cag ccc gcg ttc aag tac cag ttc gtg agg gag ccc gag      96
Pro Arg Pro Gln Pro Ala Phe Lys Tyr Gln Phe Val Arg Glu Pro Glu
                20                  25                  30 gac gag gag gaa gaa gag gag gag gaa gag gag gac gag gac gaa gac     144
Asp Glu Glu Glu Glu Glu Glu Glu Glu Glu Asp Glu Asp Glu Asp
            35                  40                  45 ctg gag gag ctg gag gtg ctg gag agg aag ccc gcc gcc ggg ctg tcc     192
Leu Glu Glu Leu Glu Val Leu Glu Arg Lys Pro Ala Ala Gly Leu Ser
        50                  55                  60 gcg gcc cca gtg ccc acc gcc cct gcc gcc ggc gcg ccc ctg atg gac     240
Ala Ala Pro Val Pro Thr Ala Pro Ala Ala Gly Ala Pro Leu Met Asp
65                  70                  75                  80 ttc gga aat gac ttc gtg ccg ccg gcg ccc cgg gga ccc ctg ccg gcc     288
Phe Gly Asn Asp Phe Val Pro Pro Ala Pro Arg Gly Pro Leu Pro Ala
                85                  90                  95 gct ccc ccc gtc gcc ccg gag cgg cag ccg tct tgg gac ccg agc ccg     336
Ala Pro Pro Val Ala Pro Glu Arg Gln Pro Ser Trp Asp Pro Ser Pro
                100                 105                 110
```

| | | | | | | | | | | | | | | | | |
|---|---|---|---|---|---|---|---|---|---|---|---|---|---|---|---|---|
| gtg | tcg | tcg | acc | gtg | ccc | gcg | cca | tcc | ccg | ctg | tct | gct | gcc | gca | gtc | 384 |
| Val | Ser | Ser | Thr | Val | Pro | Ala | Pro | Ser | Pro | Leu | Ser | Ala | Ala | Ala | Val | |
| | 115 | | | | 120 | | | | | 125 | | | | | | |
| tcg | ccc | tcc | aag | ctc | cct | gag | gac | gac | gag | cct | ccg | gcc | cgg | cct | ccc | 432 |
| Ser | Pro | Ser | Lys | Leu | Pro | Glu | Asp | Asp | Glu | Pro | Pro | Ala | Arg | Pro | Pro | |
| 130 | | | | | 135 | | | | | 140 | | | | | | |
| cct | cct | ccc | ccg | gcc | agc | gtg | agc | ccc | cag | gca | gag | ccc | gtg | tgg | acc | 480 |
| Pro | Pro | Pro | Ala | Ser | Val | Ser | Pro | Gln | Ala | Glu | Pro | Val | Trp | Thr | | |
| 145 | | | | 150 | | | | | 155 | | | | | 160 | | |
| ccg | cca | gcc | ccg | gct | ccc | gcc | gcg | ccc | ccc | tcc | acc | ccg | gcc | gcg | ccc | 528 |
| Pro | Pro | Ala | Pro | Ala | Pro | Ala | Ala | Pro | Pro | Ser | Thr | Pro | Ala | Ala | Pro | |
| | | 165 | | | | | 170 | | | | | 175 | | | | |
| aag | cgc | agg | ggc | tcc | tcg | ggc | tca | gtg | gat | gag | acc | ctt | ttt | gct | ctt | 576 |
| Lys | Arg | Arg | Gly | Ser | Ser | Gly | Ser | Val | Asp | Glu | Thr | Leu | Phe | Ala | Leu | |
| | | 180 | | | | | 185 | | | | | 190 | | | | |
| cct | gct | gca | tct | gag | cct | gtg | ata | cgc | tcc | tct | gca | gaa | aat | atg | gac | 624 |
| Pro | Ala | Ala | Ser | Glu | Pro | Val | Ile | Arg | Ser | Ser | Ala | Glu | Asn | Met | Asp | |
| | | | 195 | | | | | 200 | | | | | 205 | | | |
| ttg | aag | gag | cag | cca | ggt | aac | act | att | tcg | gct | ggt | caa | gag | gat | ttc | 672 |
| Leu | Lys | Glu | Gln | Pro | Gly | Asn | Thr | Ile | Ser | Ala | Gly | Gln | Glu | Asp | Phe | |
| 210 | | | | | 215 | | | | | 220 | | | | | | |
| cca | tct | gtc | ctg | ctt | gaa | act | gct | gct | tct | ctt | cct | tct | ctg | tct | cct | 720 |
| Pro | Ser | Val | Leu | Leu | Glu | Thr | Ala | Ala | Ser | Leu | Pro | Ser | Leu | Ser | Pro | |
| 225 | | | | | 230 | | | | | 235 | | | | | 240 | |
| ctc | tca | gcc | gct | tct | ttc | aaa | gaa | cat | gaa | tac | ctt | ggt | aat | ttg | tca | 768 |
| Leu | Ser | Ala | Ala | Ser | Phe | Lys | Glu | His | Glu | Tyr | Leu | Gly | Asn | Leu | Ser | |
| | | | | 245 | | | | | 250 | | | | | 255 | | |
| aca | gta | tta | ccc | act | gaa | gga | aca | ctt | caa | gaa | aat | gtc | agt | gaa | gct | 816 |
| Thr | Val | Leu | Pro | Thr | Glu | Gly | Thr | Leu | Gln | Glu | Asn | Val | Ser | Glu | Ala | |
| | | | 260 | | | | | 265 | | | | | 270 | | | |
| tct | aaa | gag | gtc | tca | gag | aag | gca | aaa | act | cta | ctc | ata | gat | aga | gat | 864 |
| Ser | Lys | Glu | Val | Ser | Glu | Lys | Ala | Lys | Thr | Leu | Leu | Ile | Asp | Arg | Asp | |
| | | 275 | | | | | 280 | | | | | 285 | | | | |
| tta | aca | gag | ttt | tca | gaa | tta | gaa | tac | tca | gaa | atg | gga | tca | tcg | ttc | 912 |
| Leu | Thr | Glu | Phe | Ser | Glu | Leu | Glu | Tyr | Ser | Glu | Met | Gly | Ser | Ser | Phe | |
| | 290 | | | | | 295 | | | | | 300 | | | | | |
| agt | gtc | tct | cca | aaa | gca | gaa | tct | gcc | gta | ata | gta | gca | aat | cct | agg | 960 |
| Ser | Val | Ser | Pro | Lys | Ala | Glu | Ser | Ala | Val | Ile | Val | Ala | Asn | Pro | Arg | |
| 305 | | | | | 310 | | | | | 315 | | | | | 320 | |
| gaa | gaa | ata | atc | gtg | aaa | aat | aaa | gat | gaa | gaa | gag | aag | tta | gtt | agt | 1008 |
| Glu | Glu | Ile | Ile | Val | Lys | Asn | Lys | Asp | Glu | Glu | Glu | Lys | Leu | Val | Ser | |
| | | | | 325 | | | | | 330 | | | | | 335 | | |
| aat | aac | atc | ctt | cat | aat | caa | caa | gag | tta | cct | aca | gct | ctt | act | aaa | 1056 |
| Asn | Asn | Ile | Leu | His | Asn | Gln | Gln | Glu | Leu | Pro | Thr | Ala | Leu | Thr | Lys | |
| | | | 340 | | | | | 345 | | | | | 350 | | | |
| ttg | gtt | aaa | gag | gat | gaa | gtt | gtg | tct | tca | gaa | aaa | gca | aaa | gac | agt | 1104 |
| Leu | Val | Lys | Glu | Asp | Glu | Val | Val | Ser | Ser | Glu | Lys | Ala | Lys | Asp | Ser | |
| | | 355 | | | | | 360 | | | | | 365 | | | | |
| ttt | aat | gaa | aag | aga | gtt | gca | gtg | gaa | gct | cct | atg | agg | gag | gaa | tat | 1152 |
| Phe | Asn | Glu | Lys | Arg | Val | Ala | Val | Glu | Ala | Pro | Met | Arg | Glu | Glu | Tyr | |
| | 370 | | | | | 375 | | | | | 380 | | | | | |
| gca | gac | ttc | aaa | cca | ttt | gag | cga | gta | tgg | gaa | gtg | aaa | gat | agt | aag | 1200 |
| Ala | Asp | Phe | Lys | Pro | Phe | Glu | Arg | Val | Trp | Glu | Val | Lys | Asp | Ser | Lys | |
| 385 | | | | | 390 | | | | | 395 | | | | | 400 | |
| gaa | gat | agt | gat | atg | ttg | gct | gct | gga | ggt | aaa | atc | gag | agc | aac | ttg | 1248 |
| Glu | Asp | Ser | Asp | Met | Leu | Ala | Ala | Gly | Gly | Lys | Ile | Glu | Ser | Asn | Leu | |
| | | | | 405 | | | | | 410 | | | | | 415 | | |
| gaa | agt | aaa | gtg | gat | aaa | aaa | tgt | ttt | gca | gat | agc | ctt | gag | caa | act | 1296 |
| Glu | Ser | Lys | Val | Asp | Lys | Lys | Cys | Phe | Ala | Asp | Ser | Leu | Glu | Gln | Thr | |
| | | | 420 | | | | | 425 | | | | | 430 | | | |

| | | |
|---|---|---|
| aat cac gaa aaa gat agt gag agt agt aat gat gat act tct ttc ccc<br>Asn His Glu Lys Asp Ser Glu Ser Ser Asn Asp Asp Thr Ser Phe Pro<br>435                  440                    445 | | 1344 |
| agt acg cca gaa ggt ata aag gat cgt tca gga gca tat atc aca tgt<br>Ser Thr Pro Glu Gly Ile Lys Asp Arg Ser Gly Ala Tyr Ile Thr Cys<br>    450                  455                  460 | | 1392 |
| gct ccc ttt aac cca gca gca act gag agc att gca aca aac att ttt<br>Ala Pro Phe Asn Pro Ala Ala Thr Glu Ser Ile Ala Thr Asn Ile Phe<br>465                  470                  475                480 | | 1440 |
| cct ttg tta gga gat cct act tca gaa aat aag acc gat gaa aaa aaa<br>Pro Leu Leu Gly Asp Pro Thr Ser Glu Asn Lys Thr Asp Glu Lys Lys<br>            485                  490                495 | | 1488 |
| ata gaa gaa aag aag gcc caa ata gta aca gag aag aat act agc acc<br>Ile Glu Glu Lys Lys Ala Gln Ile Val Thr Glu Lys Asn Thr Ser Thr<br>500                  505                  510 | | 1536 |
| aaa aca tca aac cct ttt ctt gta gca gca cag gat tct gag aca gat<br>Lys Thr Ser Asn Pro Phe Leu Val Ala Ala Gln Asp Ser Glu Thr Asp<br>    515                  520                  525 | | 1584 |
| tat gtc aca aca gat aat tta aca aag gtg act gag gaa gtc gtg gca<br>Tyr Val Thr Thr Asp Asn Leu Thr Lys Val Thr Glu Glu Val Val Ala<br>            530                  535                540 | | 1632 |
| aac atg cct gaa ggc ctg act cca gat tta gta cag gaa gca tgt gaa<br>Asn Met Pro Glu Gly Leu Thr Pro Asp Leu Val Gln Glu Ala Cys Glu<br>545                  550                  555                560 | | 1680 |
| agt gaa ttg aat gaa gtt act ggt aca aag att gct tat gaa aca aaa<br>Ser Glu Leu Asn Glu Val Thr Gly Thr Lys Ile Ala Tyr Glu Thr Lys<br>            565                  570                575 | | 1728 |
| atg gac ttg gtt caa aca tca gaa gtt atg caa gag tca ctc tat cct<br>Met Asp Leu Val Gln Thr Ser Glu Val Met Gln Glu Ser Leu Tyr Pro<br>                580                  585                590 | | 1776 |
| gca gca cag ctt tgc cca tca ttt gaa gag tca gaa gct act cct tca<br>Ala Ala Gln Leu Cys Pro Ser Phe Glu Glu Ser Glu Ala Thr Pro Ser<br>595                  600                  605 | | 1824 |
| cca gtt ttg cct gac att gtt atg gaa gca cca ttg aat tct gca gtt<br>Pro Val Leu Pro Asp Ile Val Met Glu Ala Pro Leu Asn Ser Ala Val<br>    610                  615                  620 | | 1872 |
| cct agt gct ggt gct tcc gtg ata cag ccc agc tca tca cca tta gaa<br>Pro Ser Ala Gly Ala Ser Val Ile Gln Pro Ser Ser Ser Pro Leu Glu<br>625                  630                  635                640 | | 1920 |
| gct tct tca gtt aat tat gaa agc ata aaa cat gag cct gaa aac ccc<br>Ala Ser Ser Val Asn Tyr Glu Ser Ile Lys His Glu Pro Glu Asn Pro<br>            645                  650                655 | | 1968 |
| cca cca tat gaa gag gcc atg agt gta tca cta aaa aaa gta tca gga<br>Pro Pro Tyr Glu Glu Ala Met Ser Val Ser Leu Lys Lys Val Ser Gly<br>                660                  665                670 | | 2016 |
| ata aag gaa gaa att aaa gag cct gaa aat att aat gca gct ctt caa<br>Ile Lys Glu Glu Ile Lys Glu Pro Glu Asn Ile Asn Ala Ala Leu Gln<br>675                  680                  685 | | 2064 |
| gaa aca gaa gct cct tat ata tct att gca tgt gat tta att aaa gaa<br>Glu Thr Glu Ala Pro Tyr Ile Ser Ile Ala Cys Asp Leu Ile Lys Glu<br>    690                  695                  700 | | 2112 |
| aca aag ctt tct gct gaa cca gct ccg gat ttc tct gat tat tca gaa<br>Thr Lys Leu Ser Ala Glu Pro Ala Pro Asp Phe Ser Asp Tyr Ser Glu<br>705                  710                  715                720 | | 2160 |
| atg gca aaa gtt gaa cag cca gtg cct gat cat tct gag cta gtt gaa<br>Met Ala Lys Val Glu Gln Pro Val Pro Asp His Ser Glu Leu Val Glu<br>            725                  730                735 | | 2208 |
| gat tcc tca cct gat tct gaa cca gtt gac tta ttt agt gat gat tca<br>Asp Ser Ser Pro Asp Ser Glu Pro Val Asp Leu Phe Ser Asp Asp Ser<br>                740                  745                750 | | 2256 |

| | | |
|---|---|---|
| ata cct gac gtt cca caa aaa caa gat gaa act gtg atg ctt gtg aaa<br>Ile Pro Asp Val Pro Gln Lys Gln Asp Glu Thr Val Met Leu Val Lys<br>     755                    760                   765 | | 2304 |
| gaa agt ctc act gag act tca ttt gag tca atg ata gaa tat gaa aat<br>Glu Ser Leu Thr Glu Thr Ser Phe Glu Ser Met Ile Glu Tyr Glu Asn<br>770                   775                    780 | | 2352 |
| aag gaa aaa ctc agt gct ttg cca cct gag gga gga aag cca tat ttg<br>Lys Glu Lys Leu Ser Ala Leu Pro Pro Glu Gly Gly Lys Pro Tyr Leu<br>785                   790                  795                800 | | 2400 |
| gaa tct ttt aag ctc agt tta gat aac aca aaa gat acc ctg tta cct<br>Glu Ser Phe Lys Leu Ser Leu Asp Asn Thr Lys Asp Thr Leu Leu Pro<br>                  805                  810                815 | | 2448 |
| gat gaa gtt tca aca ttg agc aaa aag gag aaa att cct ttg cag atg<br>Asp Glu Val Ser Thr Leu Ser Lys Lys Glu Lys Ile Pro Leu Gln Met<br>             820                  825                830 | | 2496 |
| gag gag ctc agt act gca gtt tat tca aat gat gac tta ttt att tct<br>Glu Glu Leu Ser Thr Ala Val Tyr Ser Asn Asp Asp Leu Phe Ile Ser<br>        835                   840                   845 | | 2544 |
| aag gaa gca cag ata aga gaa act gaa acg ttt tca gat tca tct cca<br>Lys Glu Ala Gln Ile Arg Glu Thr Glu Thr Phe Ser Asp Ser Ser Pro<br>850                   855                    860 | | 2592 |
| att gaa att ata gat gag ttc cct aca ttg atc agt tct aaa act gat<br>Ile Glu Ile Ile Asp Glu Phe Pro Thr Leu Ile Ser Ser Lys Thr Asp<br>865                   870                  875                880 | | 2640 |
| tca ttt tct aaa tta gcc agg gaa tat act gac cta gaa gta tcc cac<br>Ser Phe Ser Lys Leu Ala Arg Glu Tyr Thr Asp Leu Glu Val Ser His<br>                  885                  890                895 | | 2688 |
| aaa agt gaa att gct aat gcc ccg gat gga gct ggg tca ttg cct tgc<br>Lys Ser Glu Ile Ala Asn Ala Pro Asp Gly Ala Gly Ser Leu Pro Cys<br>             900                    905                910 | | 2736 |
| aca gaa ttg ccc cat gac ctt tct ttg aag aac ata caa ccc aaa gtt<br>Thr Glu Leu Pro His Asp Leu Ser Leu Lys Asn Ile Gln Pro Lys Val<br>        915                   920                   925 | | 2784 |
| gaa gag aaa atc agt ttc tca gat gac ttt tct aaa aat ggg tct gct<br>Glu Glu Lys Ile Ser Phe Ser Asp Asp Phe Ser Lys Asn Gly Ser Ala<br>930                   935                    940 | | 2832 |
| aca tca aag gtg ctc tta ttg cct cca gat gtt tct gct ttg gcc act<br>Thr Ser Lys Val Leu Leu Leu Pro Pro Asp Val Ser Ala Leu Ala Thr<br>945                   950                  955                960 | | 2880 |
| caa gca gag ata gag agc ata gtt aaa ccc aaa gtt ctt gtg aaa gaa<br>Gln Ala Glu Ile Glu Ser Ile Val Lys Pro Lys Val Leu Val Lys Glu<br>             965                    970                975 | | 2928 |
| gct gag aaa aaa ctt cct tcc gat aca gaa aaa gag gac aga tca cca<br>Ala Glu Lys Lys Leu Pro Ser Asp Thr Glu Lys Glu Asp Arg Ser Pro<br>                  980                  985                990 | | 2976 |
| tct gct ata ttt tca gca gag ctg agt aaa act tca gtt gtt gac ctc<br>Ser Ala Ile Phe Ser Ala Glu Leu Ser Lys Thr Ser Val Val Asp Leu<br>        995                  1000                1005 | | 3024 |
| ctg tac tgg aga gac att aag aag act gga gtg gtg ttt ggt gcc<br>Leu Tyr Trp Arg Asp Ile Lys Lys Thr Gly Val Val Phe Gly Ala<br>1010                   1015                1020 | | 3069 |
| agc cta ttc ctg ctg ctt tca ttg aca gta ttc agc att gtg agc<br>Ser Leu Phe Leu Leu Leu Ser Leu Thr Val Phe Ser Ile Val Ser<br>     1025                 1030                1035 | | 3114 |
| gta aca gcc tac att gcc ttg gcc ctg ctc tct gtg acc atc agc<br>Val Thr Ala Tyr Ile Ala Leu Ala Leu Leu Ser Val Thr Ile Ser<br>1040                   1045                1050 | | 3159 |
| ttt agg ata tac aag ggt gtg atc caa gct atc cag aaa tca gat<br>Phe Arg Ile Tyr Lys Gly Val Ile Gln Ala Ile Gln Lys Ser Asp<br>     1055                 1060                1065 | | 3204 |

```
gaa ggc cac cca ttc agg gca tat ctg gaa tct gaa gtt gct ata      3249
Glu Gly His Pro Phe Arg Ala Tyr Leu Glu Ser Glu Val Ala Ile
        1070                1075                1080 tct gag gag ttg gtt cag aag tac agt aat tct gct ctt ggt cat      3294
Ser Glu Glu Leu Val Gln Lys Tyr Ser Asn Ser Ala Leu Gly His
    1085                1090                1095 gtg aac tgc acg ata aag gaa ctc agg cgc ctc ttc tta gtt gat      3339
Val Asn Cys Thr Ile Lys Glu Leu Arg Arg Leu Phe Leu Val Asp
1100                1105                1110 gat tta gtt gat tct ctg aag ttt gca gtg ttg atg tgg gta ttt      3384
Asp Leu Val Asp Ser Leu Lys Phe Ala Val Leu Met Trp Val Phe
        1115                1120                1125 acc tat gtt ggt gcc ttg ttt aat ggt ctg aca cta ctg att ttg      3429
Thr Tyr Val Gly Ala Leu Phe Asn Gly Leu Thr Leu Leu Ile Leu
    1130                1135                1140 gct ctc att tca ctc ttc agt gtt cct gtt att tat gaa cgg cat      3474
Ala Leu Ile Ser Leu Phe Ser Val Pro Val Ile Tyr Glu Arg His
1145                1150                1155 cag gca cag ata gat cat tat cta gga ctt gca aat aag aat gtt      3519
Gln Ala Gln Ile Asp His Tyr Leu Gly Leu Ala Asn Lys Asn Val
        1160                1165                1170 aaa gat gct atg gct aaa atc caa gca aaa atc cct gga ttg aag      3564
Lys Asp Ala Met Ala Lys Ile Gln Ala Lys Ile Pro Gly Leu Lys
    1175                1180                1185 cgc aaa gct gaa tga aaacgcccaa aataattagt aggagttcat ctttaaaggg  3619
Arg Lys Ala Glu
1190 gatattcatt tgattatacg ggggagggtc agggaagaac gaaccttgac gttgcagtgc 3679 agtttcacag atcgttgtta gatctttatt tttagccatg cactgttgtg aggaaaaatt 3739 acctgtcttg actgccatgt gttcatcatc ttaagtattg taagctgcta tgtatggatt 3799 taaaccgtaa tcatatcttt ttcctatctg aggcactggt ggaataaaaa acctgtatat 3859 tttactttgt tgcagatagt cttgccgcat cttggcaagt tgcagagatg gtggagctag 3919

<210> SEQ ID NO 2
<211> LENGTH: 1192
<212> TYPE: PRT
<213> ORGANISM: Homo sapiens

<400> SEQUENCE: 2

Met Glu Asp Leu Asp Gln Ser Pro Leu Val Ser Ser Asp Ser Pro
1               5                   10                  15

Pro Arg Pro Gln Pro Ala Phe Lys Tyr Gln Phe Val Arg Glu Pro
            20                  25                  30

Asp Glu Glu Glu Glu Glu Glu Glu Glu Asp Glu Asp Glu Asp
        35                  40                  45

Leu Glu Glu Leu Glu Val Leu Glu Arg Lys Pro Ala Ala Gly Leu Ser
    50                  55                  60

Ala Ala Pro Val Pro Thr Ala Pro Ala Gly Ala Pro Leu Met Asp
65                  70                  75                  80

Phe Gly Asn Asp Phe Val Pro Pro Ala Pro Arg Gly Pro Leu Pro Ala
                85                  90                  95

Ala Pro Pro Val Ala Pro Glu Arg Gln Pro Ser Trp Asp Pro Ser Pro
            100                 105                 110

Val Ser Ser Thr Val Pro Ala Pro Ser Pro Leu Ser Ala Ala Ala Val
        115                 120                 125

Ser Pro Ser Lys Leu Pro Glu Asp Asp Glu Pro Pro Ala Arg Pro Pro
```

-continued

```
            130                 135                 140
Pro Pro Pro Pro Ala Ser Val Ser Pro Gln Ala Glu Pro Val Trp Thr
145                 150                 155                 160

Pro Pro Ala Pro Ala Pro Ala Ala Pro Pro Ser Thr Pro Ala Ala Pro
                165                 170                 175

Lys Arg Arg Gly Ser Ser Gly Ser Val Asp Glu Thr Leu Phe Ala Leu
                180                 185                 190

Pro Ala Ala Ser Glu Pro Val Ile Arg Ser Ser Ala Glu Asn Met Asp
                195                 200                 205

Leu Lys Glu Gln Pro Gly Asn Thr Ile Ser Ala Gly Gln Glu Asp Phe
210                 215                 220

Pro Ser Val Leu Leu Glu Thr Ala Ala Ser Leu Pro Ser Leu Ser Pro
225                 230                 235                 240

Leu Ser Ala Ala Ser Phe Lys Glu His Glu Tyr Leu Gly Asn Leu Ser
                245                 250                 255

Thr Val Leu Pro Thr Glu Gly Thr Leu Gln Glu Asn Val Ser Glu Ala
                260                 265                 270

Ser Lys Glu Val Ser Glu Lys Ala Lys Thr Leu Leu Ile Asp Arg Asp
            275                 280                 285

Leu Thr Glu Phe Ser Glu Leu Glu Tyr Ser Glu Met Gly Ser Ser Phe
            290                 295                 300

Ser Val Ser Pro Lys Ala Glu Ser Ala Val Ile Val Ala Asn Pro Arg
305                 310                 315                 320

Glu Glu Ile Ile Val Lys Asn Lys Asp Glu Glu Lys Leu Val Ser
                325                 330                 335

Asn Asn Ile Leu His Asn Gln Gln Glu Leu Pro Thr Ala Leu Thr Lys
                340                 345                 350

Leu Val Lys Glu Asp Glu Val Val Ser Ser Glu Lys Ala Lys Asp Ser
            355                 360                 365

Phe Asn Glu Lys Arg Val Ala Val Glu Ala Pro Met Arg Glu Glu Tyr
            370                 375                 380

Ala Asp Phe Lys Pro Phe Glu Arg Val Trp Glu Val Lys Asp Ser Lys
385                 390                 395                 400

Glu Asp Ser Asp Met Leu Ala Ala Gly Gly Lys Ile Glu Ser Asn Leu
                405                 410                 415

Glu Ser Lys Val Asp Lys Lys Cys Phe Ala Asp Ser Leu Glu Gln Thr
                420                 425                 430

Asn His Glu Lys Asp Ser Glu Ser Ser Asn Asp Thr Ser Phe Pro
            435                 440                 445

Ser Thr Pro Glu Gly Ile Lys Asp Arg Ser Gly Ala Tyr Ile Thr Cys
450                 455                 460

Ala Pro Phe Asn Pro Ala Ala Thr Glu Ser Ile Ala Thr Asn Ile Phe
465                 470                 475                 480

Pro Leu Leu Gly Asp Pro Thr Ser Glu Asn Lys Thr Asp Glu Lys
                485                 490                 495

Ile Glu Glu Lys Lys Ala Gln Ile Val Thr Glu Lys Asn Thr Ser Thr
            500                 505                 510

Lys Thr Ser Asn Pro Phe Leu Val Ala Ala Gln Asp Ser Glu Thr Asp
            515                 520                 525

Tyr Val Thr Thr Asp Asn Leu Thr Lys Val Thr Glu Glu Val Ala
            530                 535                 540

Asn Met Pro Glu Gly Leu Thr Pro Asp Leu Val Gln Glu Ala Cys Glu
545                 550                 555                 560
```

-continued

Ser Glu Leu Asn Glu Val Thr Gly Thr Lys Ile Ala Tyr Glu Thr Lys
            565                 570                 575

Met Asp Leu Val Gln Thr Ser Glu Val Met Gln Glu Ser Leu Tyr Pro
            580                 585                 590

Ala Ala Gln Leu Cys Pro Ser Phe Glu Glu Ser Glu Ala Thr Pro Ser
            595                 600                 605

Pro Val Leu Pro Asp Ile Val Met Glu Ala Pro Leu Asn Ser Ala Val
        610                 615                 620

Pro Ser Ala Gly Ala Ser Val Ile Gln Pro Ser Ser Pro Leu Glu
625                 630                 635                 640

Ala Ser Ser Val Asn Tyr Glu Ser Ile Lys His Glu Pro Glu Asn Pro
                645                 650                 655

Pro Pro Tyr Glu Glu Ala Met Ser Val Ser Leu Lys Lys Val Ser Gly
            660                 665                 670

Ile Lys Glu Glu Ile Lys Glu Pro Glu Asn Ile Asn Ala Ala Leu Gln
        675                 680                 685

Glu Thr Glu Ala Pro Tyr Ile Ser Ile Ala Cys Asp Leu Ile Lys Glu
        690                 695                 700

Thr Lys Leu Ser Ala Glu Pro Ala Pro Asp Phe Ser Asp Tyr Ser Glu
705                 710                 715                 720

Met Ala Lys Val Glu Gln Pro Val Pro Asp His Ser Glu Leu Val Glu
            725                 730                 735

Asp Ser Ser Pro Asp Ser Glu Pro Val Asp Leu Phe Ser Asp Asp Ser
            740                 745                 750

Ile Pro Asp Val Pro Gln Lys Gln Asp Glu Thr Val Met Leu Val Lys
        755                 760                 765

Glu Ser Leu Thr Glu Thr Ser Phe Glu Ser Met Ile Glu Tyr Glu Asn
770                 775                 780

Lys Glu Lys Leu Ser Ala Leu Pro Pro Glu Gly Gly Lys Pro Tyr Leu
785                 790                 795                 800

Glu Ser Phe Lys Leu Ser Leu Asp Asn Thr Lys Asp Thr Leu Leu Pro
                805                 810                 815

Asp Glu Val Ser Thr Leu Ser Lys Lys Glu Lys Ile Pro Leu Gln Met
            820                 825                 830

Glu Glu Leu Ser Thr Ala Val Tyr Ser Asn Asp Asp Leu Phe Ile Ser
            835                 840                 845

Lys Glu Ala Gln Ile Arg Glu Thr Glu Thr Phe Ser Asp Ser Ser Pro
850                 855                 860

Ile Glu Ile Ile Asp Glu Phe Pro Thr Leu Ile Ser Ser Lys Thr Asp
865                 870                 875                 880

Ser Phe Ser Lys Leu Ala Arg Glu Tyr Thr Asp Leu Glu Val Ser His
                885                 890                 895

Lys Ser Glu Ile Ala Asn Ala Pro Asp Gly Ala Gly Ser Leu Pro Cys
            900                 905                 910

Thr Glu Leu Pro His Asp Leu Ser Leu Lys Asn Ile Gln Pro Lys Val
        915                 920                 925

Glu Glu Lys Ile Ser Phe Ser Asp Asp Phe Ser Lys Asn Gly Ser Ala
        930                 935                 940

Thr Ser Lys Val Leu Leu Leu Pro Pro Asp Val Ser Ala Leu Ala Thr
945                 950                 955                 960

Gln Ala Glu Ile Glu Ser Ile Val Lys Pro Lys Val Leu Val Lys Glu
                965                 970                 975

Ala Glu Lys Lys Leu Pro Ser Asp Thr Glu Lys Glu Asp Arg Ser Pro
            980                 985                 990

-continued

```
Ser Ala Ile Phe Ser Ala Glu Leu  Ser Lys Thr Ser Val  Val Asp Leu
        995                 1000                 1005

Leu Tyr Trp Arg Asp Ile Lys  Lys Thr Gly Val Val  Phe Gly Ala
    1010                1015                1020

Ser Leu Phe Leu Leu Leu Ser  Leu Thr Val Phe Ser  Ile Val Ser
    1025                1030                1035

Val Thr Ala Tyr Ile Ala Leu  Ala Leu Leu Ser Val  Thr Ile Ser
    1040                1045                1050

Phe Arg Ile Tyr Lys Gly Val  Ile Gln Ala Ile Gln  Lys Ser Asp
    1055                1060                1065

Glu Gly His Pro Phe Arg Ala  Tyr Leu Glu Ser Glu  Val Ala Ile
    1070                1075                1080

Ser Glu Glu Leu Val Gln Lys  Tyr Ser Asn Ser Ala  Leu Gly His
    1085                1090                1095

Val Asn Cys Thr Ile Lys Glu  Leu Arg Arg Leu Phe  Leu Val Asp
    1100                1105                1110

Asp Leu Val Asp Ser Leu Lys  Phe Ala Val Leu Met  Trp Val Phe
    1115                1120                1125

Thr Tyr Val Gly Ala Leu Phe  Asn Gly Leu Thr Leu  Leu Ile Leu
    1130                1135                1140

Ala Leu Ile Ser Leu Phe Ser  Val Pro Val Ile Tyr  Glu Arg His
    1145                1150                1155

Gln Ala Gln Ile Asp His Tyr  Leu Gly Leu Ala Asn  Lys Asn Val
    1160                1165                1170

Lys Asp Ala Met Ala Lys Ile  Gln Ala Lys Ile Pro  Gly Leu Lys
    1175                1180                1185

Arg Lys Ala Glu
    1190

<210> SEQ ID NO 3
<211> LENGTH: 819
<212> TYPE: PRT
<213> ORGANISM: Homo sapiens
<220> FEATURE:
<221> NAME/KEY: PEPTIDE
<222> LOCATION: (1)..(819)
<223> OTHER INFORMATION: human Nig

<400> SEQUENCE: 3

Asp Glu Thr Leu Phe Ala Leu Pro Ala Ala Ser Glu Pro Val Ile Arg
1               5                   10                  15

Ser Ser Ala Glu Asn Met Asp Leu Lys Glu Gln Pro Gly Asn Thr Ile
            20                  25                  30

Ser Ala Gly Gln Glu Asp Phe Pro Ser Val Leu Leu Thr Ala Ala
        35                  40                  45

Ser Leu Pro Ser Leu Ser Pro Leu Ser Ala Ala Ser Phe Lys Glu His
    50                  55                  60

Glu Tyr Leu Gly Asn Leu Ser Thr Val Leu Pro Thr Glu Gly Thr Leu
65                  70                  75                  80

Gln Glu Asn Val Ser Glu Ala Ser Lys Glu Val Ser Glu Lys Ala Lys
                85                  90                  95

Thr Leu Leu Ile Asp Arg Asp Leu Thr Glu Phe Ser Glu Leu Glu Tyr
            100                 105                 110

Ser Glu Met Gly Ser Ser Phe Ser Val Ser Pro Lys Ala Glu Ser Ala
        115                 120                 125

Val Ile Val Ala Asn Pro Arg Glu Glu Ile Ile Val Lys Asn Lys Asp
```

-continued

```
            130                 135                 140
Glu Glu Glu Lys Leu Val Ser Asn Asn Ile Leu His Asn Gln Gln Glu
145                 150                 155                 160

Leu Pro Thr Ala Leu Thr Lys Leu Val Lys Glu Asp Glu Val Val Ser
                165                 170                 175

Ser Glu Lys Ala Lys Asp Ser Phe Asn Glu Lys Arg Val Ala Val Glu
                180                 185                 190

Ala Pro Met Arg Glu Gly Tyr Ala Asp Phe Lys Pro Phe Glu Arg Val
                195                 200                 205

Trp Glu Val Lys Asp Ser Lys Glu Asp Ser Asp Met Leu Ala Ala Gly
210                 215                 220

Gly Lys Ile Glu Ser Asn Leu Glu Ser Lys Val Asp Lys Lys Cys Phe
225                 230                 235                 240

Ala Asp Ser Leu Glu Gln Thr Asn His Glu Lys Asp Ser Glu Ser Ser
                245                 250                 255

Asn Asp Asp Thr Ser Phe Pro Ser Thr Pro Glu Gly Ile Lys Asp Arg
                260                 265                 270

Ser Gly Ala Tyr Ile Thr Cys Ala Pro Phe Asn Pro Ala Ala Thr Glu
                275                 280                 285

Ser Ile Ala Thr Asn Ile Phe Pro Leu Leu Gly Asp Pro Thr Ser Glu
290                 295                 300

Asn Lys Thr Asp Glu Lys Lys Ile Glu Glu Lys Ala Gln Ile Val
305                 310                 315                 320

Thr Glu Lys Asn Thr Ser Thr Lys Thr Ser Asn Pro Phe Leu Val Ala
                325                 330                 335

Ala Gln Asp Ser Glu Thr Asp Tyr Val Thr Thr Asp Asn Leu Thr Lys
                340                 345                 350

Val Thr Glu Glu Val Val Ala Asn Met Pro Glu Gly Leu Thr Pro Asp
                355                 360                 365

Leu Val Gln Glu Ala Cys Glu Ser Glu Leu Asn Glu Val Thr Gly Thr
370                 375                 380

Lys Ile Ala Tyr Glu Thr Lys Met Asp Leu Val Gln Thr Ser Glu Val
385                 390                 395                 400

Met Gln Glu Ser Leu Tyr Pro Ala Ala Gln Leu Cys Pro Ser Phe Glu
                405                 410                 415

Glu Ser Glu Ala Thr Pro Ser Pro Val Leu Pro Asp Ile Val Met Glu
                420                 425                 430

Ala Pro Leu Asn Ser Ala Val Pro Ser Ala Gly Ala Ser Val Ile Gln
                435                 440                 445

Pro Ser Ser Ser Pro Leu Glu Ala Ser Ser Val Asn Tyr Glu Ser Ile
450                 455                 460

Lys His Glu Pro Glu Asn Pro Pro Tyr Glu Glu Ala Met Ser Val
465                 470                 475                 480

Ser Leu Lys Lys Val Ser Gly Ile Lys Glu Ile Lys Glu Pro Glu
                485                 490                 495

Asn Ile Asn Ala Ala Leu Gln Glu Thr Glu Ala Pro Tyr Ile Ser Ile
                500                 505                 510

Ala Cys Asp Leu Ile Lys Glu Thr Lys Leu Ser Ala Glu Pro Ala Pro
                515                 520                 525

Asp Phe Ser Asp Tyr Ser Glu Met Ala Lys Val Glu Gln Pro Val Pro
                530                 535                 540

Asp His Ser Glu Leu Val Glu Asp Ser Ser Pro Asp Ser Glu Pro Val
545                 550                 555                 560
```

-continued

```
Asp Leu Phe Ser Asp Ser Ile Pro Asp Val Pro Gln Lys Gln Asp
                565                 570                 575

Glu Thr Val Met Leu Val Lys Glu Ser Leu Thr Glu Thr Ser Phe Glu
            580                 585                 590

Ser Met Ile Glu Tyr Glu Asn Lys Glu Lys Leu Ser Ala Leu Pro Pro
        595                 600                 605

Glu Gly Gly Lys Pro Tyr Leu Glu Ser Phe Lys Leu Ser Leu Asp Asn
    610                 615                 620

Thr Lys Asp Thr Leu Leu Pro Asp Glu Val Ser Thr Leu Ser Lys Lys
625                 630                 635                 640

Glu Lys Ile Pro Leu Gln Met Glu Glu Leu Ser Thr Ala Val Tyr Ser
                645                 650                 655

Asn Asp Asp Leu Phe Ile Ser Lys Glu Ala Gln Ile Arg Glu Thr Glu
            660                 665                 670

Thr Phe Ser Asp Ser Ser Pro Ile Glu Ile Asp Glu Phe Pro Thr
        675                 680                 685

Leu Ile Ser Ser Lys Thr Asp Ser Phe Ser Lys Leu Ala Arg Glu Tyr
    690                 695                 700

Thr Asp Leu Glu Val Ser His Lys Ser Glu Ile Ala Asn Ala Pro Asp
705                 710                 715                 720

Gly Ala Gly Ser Leu Pro Cys Thr Glu Leu Pro His Asp Leu Ser Leu
                725                 730                 735

Lys Asn Ile Gln Pro Lys Val Glu Glu Lys Ile Ser Phe Ser Asp Asp
            740                 745                 750

Phe Ser Lys Asn Gly Ser Ala Thr Ser Lys Val Leu Leu Leu Pro Pro
        755                 760                 765

Asp Val Ser Ala Leu Ala Thr Gln Ala Glu Ile Glu Ser Ile Val Lys
    770                 775                 780

Pro Lys Val Leu Val Lys Glu Ala Lys Lys Leu Pro Ser Asp Thr
785                 790                 795                 800

Glu Lys Glu Asp Arg Ser Pro Ser Ala Ile Phe Ser Ala Glu Leu Ser
                805                 810                 815

Lys Thr Ser

<210> SEQ ID NO 4
<211> LENGTH: 246
<212> TYPE: PRT
<213> ORGANISM: Mus musculus

<400> SEQUENCE: 4

Met Glu Phe Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Trp Met Ser Trp Val Arg Gln Ala Pro Gly Lys Gly Leu
    50                  55                  60

Glu Trp Val Ala Thr Ile Lys Gln Asp Gly Ser Gln Lys Asn Tyr Val
65                  70                  75                  80

Asp Ser Val Lys Gly Arg Phe Thr Ile Ser Arg Asp Asn Ala Lys Asn
                85                  90                  95

Ser Leu Tyr Leu Arg Leu Asn Ser Leu Arg Ala Glu Asp Thr Ala Val
            100                 105                 110

Tyr Tyr Cys Ala Thr Glu Leu Phe Asp Leu Trp Gly Arg Gly Ser Leu
```

```
               115                 120                 125
Val Thr Val Ser Ser Ala Ser Thr Lys Gly Pro Ser Val Phe Pro Leu
130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Arg Val Glu Pro Lys Ser Cys Asp Lys Thr His
225                 230                 235                 240

Thr Cys Pro Pro Cys Pro
                245

<210> SEQ ID NO 5
<211> LENGTH: 246
<212> TYPE: PRT
<213> ORGANISM: Mus musculus

<400> SEQUENCE: 5

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Cys Asp Arg Leu Leu Ser Cys Arg
        35                  40                  45

Ala Ser Gln Ser Val Ser Ser Tyr Leu Ala Trp Tyr Gln Gln Lys Pro
50                  55                  60

Cys Asp Arg Leu Gly Gln Ala Pro Arg Leu Leu Ile Tyr Asp Ala Ser
65                  70                  75                  80

Asn Arg Ala Thr Gly Ile Pro Ala Arg Phe Ser Gly Ser Gly Ser Gly
                85                  90                  95

Thr Asp Phe Thr Leu Thr Ile Ser Ser Leu Glu Pro Cys Asp Arg Leu
            100                 105                 110

Glu Asp Phe Ala Val Tyr Tyr Cys Gln Gln Arg Ser Asn Trp Pro Ile
        115                 120                 125

Thr Phe Gly Gln Gly Thr Arg Leu Glu Ile Lys Arg Thr Val Ala Ala
130                 135                 140

Pro Ser Val Phe Ile Phe Pro Pro Ser Asp Glu Gln Leu Lys Ser Gly
145                 150                 155                 160

Thr Ala Ser Val Val Cys Leu Leu Asn Asn Phe Tyr Pro Arg Glu Ala
                165                 170                 175

Lys Val Gln Trp Lys Val Asp Asn Ala Leu Gln Ser Gly Asn Ser Gln
            180                 185                 190

Glu Ser Val Thr Glu Gln Asp Ser Lys Asp Ser Thr Tyr Ser Leu Ser
        195                 200                 205

Ser Thr Leu Thr Leu Ser Lys Ala Asp Tyr Glu Lys His Lys Val Tyr
    210                 215                 220

Ala Cys Glu Val Thr His Gln Gly Leu Ser Ser Pro Val Thr Lys Ser
225                 230                 235                 240

Phe Asn Arg Gly Glu Cys
```

```
                        245

<210> SEQ ID NO 6
<211> LENGTH: 741
<212> TYPE: DNA
<213> ORGANISM: Mus musculus

<400> SEQUENCE: 6
atggagtttg ggctgagctg ggttttcctt gttgctattt tagaaggtgt ccagtgtgag    60
gtgcagctgg tggagtctgg gggaggcttg gtccagcctg gggggtccct gagactctcc   120
tgtgcagctt ctggattcac ctttagtaac tattggatga gctgggtccg ccaggctccg   180
gggaaagggc tggagtgggt ggccaccata agcaagatg gaagtcagaa aaactatgtg   240
gactctgtga agggccgatt caccatctcc agagacaacg ccaagaactc actgtatctg   300
cgattgaaca gcctgagagc cgaggacacg gctgtgtatt actgtgcgac tgaactcttc   360
gatctctggg gccgtggctc cctggtcacc gtctcctcag cctccaccaa gggcccatcg   420
gtcttccccc tggcaccctc ctccaagagc acctctgggg gcacagcggc cctgggctgc   480
ctggtcaagg actacttccc cgaaccggtg acggtgtcgt ggaactcagg cgccctgacc   540
agcggcgtgc acaccttccc ggctgtccta cagtcctcag gactctactc cctcagcagc   600
gtggtgaccg tgccctccag cagcttgggc acccagacct acatctgcaa cgtgaatcac   660
aagcccagca acaccaaggt ggacaagaga gttgagccca atcttgtga caaaactcac   720 acatgcccac cgtgcccata a                                             741

<210> SEQ ID NO 7
<211> LENGTH: 705
<212> TYPE: DNA
<213> ORGANISM: Mus musculus

<400> SEQUENCE: 7
atggaagccc cagctcagct tctcttcctc ctgctactct ggctcccaga taccaccgga    60
gaaattgtgt tgacacagtc tccagccacc ctgtctttgt ctccagggga aagagccacc   120
ctctcctgca gggccagtca gagtgttagc agctacttag cctggtacca acagaaacct   180
ggccaggctc ccaggctcct catctatgat gcatccaaca gggccactgg catcccagcc   240
aggttcagtg gcagtgggtc tgggacagac ttcactctca ccatcagcag cctagagcct   300
gaagattttg cagtttatta ctgtcagcag cgtagcaact ggccgatcac cttcggccaa   360
gggacacgac tggagattaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaacacaaa gtctacgcct gcgaagtcac ccatcagggc   660
ctgagctcgc ccgtcacaaa gagcttcaac aggggagagt gttag                   705

<210> SEQ ID NO 8
<211> LENGTH: 10
<212> TYPE: PRT
<213> ORGANISM: Mus musculus

<400> SEQUENCE: 8

Gly Phe Thr Phe Ser Asn Tyr Trp Met Ser
1               5                   10
```

```
<210> SEQ ID NO 9
<211> LENGTH: 17
<212> TYPE: PRT
<213> ORGANISM: Mus musculus

<400> SEQUENCE: 9

Thr Ile Lys Gln Asp Gly Ser Gln Lys Asn Tyr Val Asp Ser Val Lys
1               5                   10                  15

Gly

<210> SEQ ID NO 10
<211> LENGTH: 5
<212> TYPE: PRT
<213> ORGANISM: Mus musculus

<400> SEQUENCE: 10

Glu Leu Phe Asp Leu
1               5

<210> SEQ ID NO 11
<211> LENGTH: 11
<212> TYPE: PRT
<213> ORGANISM: Mus musculus

<400> SEQUENCE: 11

Arg Ala Ser Gln Ser Val Ser Ser Tyr Leu Ala
1               5                   10

<210> SEQ ID NO 12
<211> LENGTH: 7
<212> TYPE: PRT
<213> ORGANISM: Mus musculus

<400> SEQUENCE: 12

Asp Ala Ser Asn Arg Ala Thr
1               5

<210> SEQ ID NO 13
<211> LENGTH: 9
<212> TYPE: PRT
<213> ORGANISM: Mus musculus

<400> SEQUENCE: 13

Gln Gln Arg Ser Asn Trp Pro Ile Thr
1               5

<210> SEQ ID NO 14
<211> LENGTH: 34
<212> TYPE: DNA
<213> ORGANISM: Mus musculus

<400> SEQUENCE: 14
agggccagtc agagtgttag cagctactta gcct                              34

<210> SEQ ID NO 15
<211> LENGTH: 21
<212> TYPE: DNA
<213> ORGANISM: Mus musculus

<400> SEQUENCE: 15
gatgcatcca acagggccac t                                            21

<210> SEQ ID NO 16
<211> LENGTH: 27
<212> TYPE: DNA
```

<213> ORGANISM: Mus musculus

<400> SEQUENCE: 16
cagcagcgta gcaactggcc gatcacc 27

<210> SEQ ID NO 17
<211> LENGTH: 30
<212> TYPE: DNA
<213> ORGANISM: Mus musculus

<400> SEQUENCE: 17
ggattcacct ttagtaacta ttggatgagc 30

<210> SEQ ID NO 18
<211> LENGTH: 51
<212> TYPE: DNA
<213> ORGANISM: Mus musculus

<400> SEQUENCE: 18
accataaagc aagatggaag tcagaaaaac tatgtggact ctgtgaaggg c 51

<210> SEQ ID NO 19
<211> LENGTH: 15
<212> TYPE: DNA
<213> ORGANISM: Mus musculus

<400> SEQUENCE: 19
gaactcttcg atctc 15

<210> SEQ ID NO 20
<211> LENGTH: 57
<212> TYPE: DNA
<213> ORGANISM: Mus musculus

<400> SEQUENCE: 20
atggagtttg ggctgagctg ggttttcctt gttgctattt tagaaggtgt ccagtgt 57

<210> SEQ ID NO 21
<211> LENGTH: 19
<212> TYPE: PRT
<213> ORGANISM: Mus musculus

<400> SEQUENCE: 21

Met Glu Phe Gly Leu Ser Trp Val Phe Leu Val Ala Ile Leu Glu Gly
1               5                   10                  15

Val Gln Cys

<210> SEQ ID NO 22
<211> LENGTH: 60
<212> TYPE: DNA
<213> ORGANISM: Mus musculus

<400> SEQUENCE: 22
atggaagccc cagctcagct tctcttcctc ctgctactct ggctcccaga taccaccgga 60

<210> SEQ ID NO 23
<211> LENGTH: 20
<212> TYPE: PRT
<213> ORGANISM: Mus musculus

<400> SEQUENCE: 23

Met Glu Ala Pro Ala Gln Leu Leu Phe Leu Leu Leu Leu Trp Leu Pro
1               5                   10                  15

Asp Thr Thr Gly
                20

<210> SEQ ID NO 24
<211> LENGTH: 460
<212> TYPE: PRT
<213> ORGANISM: Mus musculus

<400> SEQUENCE: 24

Met Ala Trp Val Trp Thr Leu Pro Phe Leu Met Ala Ala Gln Ser
1               5                   10                  15

Val Gln Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
            35                  40                  45

Ser Asn Tyr Trp Met Ser Trp Val Arg Gln Ala Pro Gly Lys Gly Leu
        50                  55                  60

Glu Trp Val Ala Thr Ile Lys Gln Asp Gly Ser Gln Lys Asn Tyr Val
65                  70                  75                  80

Asp Ser Val Lys Gly Arg Phe Thr Ile Ser Arg Asp Asn Ala Lys Asn
                85                  90                  95

Ser Leu Tyr Leu Arg Leu Asn Ser Leu Arg Ala Glu Asp Thr Ala Val
            100                 105                 110

Tyr Tyr Cys Ala Thr Glu Leu Phe Asp Leu Trp Gly Arg Gly Ser Leu
        115                 120                 125

Val Thr Val Ser Ser Ala Ser Thr Lys Gly Pro Ser Val Phe Pro Leu
    130                 135                 140

Ala Pro Cys Ser Arg Ser Thr Ser Glu Ser Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Lys Thr Tyr Thr Cys Asn Val Asp His Lys Pro Ser Asn
    210                 215                 220

Thr Lys Val Asp Lys Arg Val Glu Ser Lys Tyr Gly Pro Pro Cys Pro
225                 230                 235                 240

Ser Cys Pro Ala Pro Glu Phe Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Gly Leu Pro Ser Ser Ile Glu Lys Thr Ile Ser Lys Ala
            340                 345                 350

Lys Gly Gln Pro Arg Glu Pro Gln Val Tyr Thr Leu Pro Pro Ser Gln
        355                 360                 365

-continued

```
Glu Glu Met Thr Lys Asn Gln Val Ser Leu Thr Cys Leu Val Lys Gly
        370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
            405                 410                 415

Phe Phe Leu Tyr Ser Arg Leu Thr Val Asp Lys Ser Arg Trp Gln Glu
        420                 425                 430

Gly Asn Val Phe Ser Cys Ser Val Met His Glu Ala Leu His Asn His
            435                 440                 445

Tyr Thr Gln Lys Ser Leu Ser Leu Ser Leu Gly Lys
        450                 455                 460

<210> SEQ ID NO 25
<211> LENGTH: 234
<212> TYPE: PRT
<213> ORGANISM: Mus musculus

<400> SEQUENCE: 25

Met Ser Val Leu Thr Gln Val Leu Ala Leu Leu Leu Leu Trp Leu Thr
1               5                   10                  15

Gly Thr Arg Cys Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Ile Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 26
<211> LENGTH: 321
<212> TYPE: DNA
<213> ORGANISM: Mus musculus
<220> FEATURE:
<221> NAME/KEY: CDS
<222> LOCATION: (1)..(321)
```

```
<400> SEQUENCE: 26 gaa att gtg ttg aca cag tct cca gcc acc ctg tct ttg tct cca ggg      48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac      96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg ccg atc     288
Glu Asp Phe Ala Val Tyr Tyr Cys Gln Gln Arg Ser Asn Trp Pro Ile
                85                  90                  95 acc ttc ggc caa ggg aca aag ctt gaa atc aaa                         321
Thr Phe Gly Gln Gly Thr Lys Leu Glu Ile Lys
            100                 105

<210> SEQ ID NO 27
<211> LENGTH: 107
<212> TYPE: PRT
<213> ORGANISM: Mus musculus

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Lys Leu Glu Ile Lys
            100                 105

<210> SEQ ID NO 28
<211> LENGTH: 342
<212> TYPE: DNA
<213> ORGANISM: Mus musculus
<220> FEATURE:
<221> NAME/KEY: CDS
<222> LOCATION: (1)..(342)

<400> SEQUENCE: 28 gag gtg cag ctg gtg gag tct ggg gga ggc ttg gtc cag cct ggg ggg      48
Glu Val Gln Leu Val Glu Ser Gly Gly Gly Leu Val Gln Pro Gly Gly
1               5                   10                  15 tcc ctg aga ctc tcc tgt gca gct tct gga ttc acc ttt agt aac tat      96
Ser Leu Arg Leu Ser Cys Ala Ala Ser Gly Phe Thr Phe Ser Asn Tyr
            20                  25                  30 tgg atg agc tgg gtc cgc cag gct ccg ggg aaa ggg ctg gag tgg gtg     144
Trp Met Ser Trp Val Arg Gln Ala Pro Gly Lys Gly Leu Glu Trp Val
```

```
                35                  40                  45
gcc acc ata aag caa gat gga agt cag aaa aac tat gtg gac tct gtg      192
Ala Thr Ile Lys Gln Asp Gly Ser Gln Lys Asn Tyr Val Asp Ser Val
 50                  55                  60 aag ggc cga ttc acc atc tcc aga gac aac gcc aag aac tca ctg tat      240
Lys Gly Arg Phe Thr Ile Ser Arg Asp Asn Ala Lys Asn Ser Leu Tyr
 65                  70                  75                  80 ctg cga ttg aac agc ctg aga gcc gag gac acg gct gtg tat tac tgt      288
Leu Arg Leu Asn Ser Leu Arg Ala Glu Asp Thr Ala Val Tyr Tyr Cys
                 85                  90                  95 gcg act gaa ctc ttc gat ctc tgg ggc cgt ggc tcc ctg gtc acc gtc      336
Ala Thr Glu Leu Phe Asp Leu Trp Gly Arg Gly Ser Leu Val Thr Val
            100                 105                 110 tcc tca                                                              342
Ser Ser <210> SEQ ID NO 29
<211> LENGTH: 114
<212> TYPE: PRT
<213> ORGANISM: Mus musculus

<400> SEQUENCE: 29

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                20                  25                  30

Trp Met Ser Trp Val Arg Gln Ala Pro Gly Lys Gly Leu Glu Trp Val
             35                  40                  45

Ala Thr Ile Lys Gln Asp Gly Ser Gln Lys Asn Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Arg Leu Asn Ser Leu Arg Ala Glu Asp Thr Ala Val Tyr Tyr Cys
                 85                  90                  95

Ala Thr Glu Leu Phe Asp Leu Trp Gly Arg Gly Ser Leu Val Thr Val
            100                 105                 110

Ser Ser

<210> SEQ ID NO 30
<211> LENGTH: 19
<212> TYPE: PRT
<213> ORGANISM: Mus musculus

<400> SEQUENCE: 30

Met Ala Trp Val Trp Thr Leu Pro Phe Leu Met Ala Ala Ala Gln Ser
 1               5                  10                  15

Val Gln Ala

<210> SEQ ID NO 31
<211> LENGTH: 20
<212> TYPE: PRT
<213> ORGANISM: Mus musculus

<400> SEQUENCE: 31

Met Ser Val Leu Thr Gln Val Leu Ala Leu Leu Leu Leu Trp Leu Thr
 1               5                  10                  15

Gly Thr Arg Cys
            20
```

```
<210> SEQ ID NO 32
<211> LENGTH: 20
<212> TYPE: DNA
<213> ORGANISM: Artificial sequence
<220> FEATURE:
<223> OTHER INFORMATION: primer

<400> SEQUENCE: 32
tgagggaagt agggatgtgc                                                   20

<210> SEQ ID NO 33
<211> LENGTH: 20
<212> TYPE: DNA
<213> ORGANISM: Artificial sequence
<220> FEATURE:
<223> OTHER INFORMATION: primer

<400> SEQUENCE: 33
caggtgatgt acgctctgga                                                   20
```

NOGO-A BINDING MOLECULES AND PHARMACEUTICAL USE THEREOF

FIELD OF THE INVENTION

This application is a continuation of 12/740,777, filed Apr. 30, 2010 as a national phase of PCT/EP08/064501, filed Oct. 27, 2008, which claims benefit of EP Patent Application No. 07119847.7, filed Nov. 2, 2007 and U.S. Provisional Application 61/001,741, filed Nov. 2, 2007, all of which in their entirety are herein incorporated by reference.

The invention relates to improved NogoA binding molecules, such as for example, monoclonal antibodies, derivatives or Fab fragments thereof.

BACKGROUND OF THE INVENTION

Neuronal regeneration following injury in the adult central nervous system (CNS) is limited due to the presence of the inhibitory myelin environment that ensheaths axons and the formation of scar tissue. In the last few years important insights have been gained into the molecular understanding of why the CNS is unable to spontaneously repair itself following injury. Inhibitory molecules in the myelin are the major impediment for the axonal regeneration, particularly immediately after the injury. So far NogoA, Myelin-Associated Glycoprotein (MAG) and myelin-oligodendrocyte glycoprotein (OMgp) have been characterised as potent inhibitors of neurite outgrowth. In addition, myelin also contains other inhibitory components, such as chondroitin sulphate proteoglycans. Nogo-A is a member of the reticulon protein family and it has at least two biologically active and pharmacologically distinct domains termed Amino-Nogo and Nogo-66. While the receptor site for the former is not known so far, Nogo-66 inhibits neuronal growth in vitro and in vivo via the neuronal receptor NgR. In addition to Nogo-66, MAG and OMgp also bind to the NgR with high affinity and inhibit neurite outgrowth.

New research approaches currently pursued for enhancement of nerve repair include digestion of scar tissue using an enzyme chondroitinase ABC, bridging techniques using Olfactory ensheathing cells and stem cells and protein growth factors to boost neuronal growth. The blocking actions of neurite outgrowth inhibitors can be achieved by modulation of intracellular signaling mediators such as Rho, a membrane-bound guanosine triphosphatase(GTPase), which appears to be a key link in the inhibition of axonal growth. Cyclic adenosine monophosphate (cAMP) can overcome myelin associated inhibition in vitro and induce regeneration in vivo. The peptide inhibitor of the NgR receptor (NEP 1-40) can be used to induce neuronal regrowth and functional recovery in rats following spinal injury.

In addition to the use of the approaches described above, much attention has also focused upon the use of certain monoclonal antibodies to neutralize neurite growth inhibitory molecules of the central and peripheral nervous system, in particular to neutralize the neurite growth inhibitory activity of NogoA. Thus it has been shown that the monoclonal antibody IN-1 or the IN-1 Fab fragment thereof induce neurite outgrowth in vitro and enhance sprouting and regeneration in vivo (Schwab ME et al. (1996) Physiol. Rev. 76, 319-370). Alternative antibodies to IN-1 have also been described in WO2004/052932 (11C7-Ab) and WO2005/028508 (3A6-Ab). Testing different domains of the NogoA for neurite growth inhibitory activity have delineated several inhibitory domains in the molecule (Chen et al. (2000) Nature 403, 434-439; GrandPre et al., (2000) Nature 403, 439-444; Prinjha et al. (2000) Nature 403, 383-384.

Natural immunoglobulins or antibodies comprise a generally Y- shaped multimeric molecule having an antigen-binding site at the end of each upper arm. The remainder of the structure, in particular the stem of the Y mediates effector functions associated with the immunoglobulins. Antibodies consists of 2 heavy and 2 light chains. Both heavy and light chains comprise a variable domain and a constant part. An antigen binding site consists of the variable domain of a heavy chain associated with the variable domain of a light chain. The variable domains of the heavy and light chains have the same general structure. More particularly, the antigen binding characteristics of an antibody are essentially determined by 3 specific regions in the variable domain of the heavy and light chains which are called hypervariable, regions or complementarity determining regions (CDRs). These 3 hypervariable regions alternate with 4 framework regions (FRs) whose sequences are relatively conserved and which are not directly involved in binding. The CDRs form loops and are held in close proximity by the framework regions which largely adopt a β-sheet conformation. The CDRs of a heavy chain together with the CDRs of the associated light chain essentially constitute the antigen binding site of the antibody molecule. The determination as to what constitutes an FR or a CDR region is usually made by comparing the amino acid sequence of a number of antibodies raised in the same species. The general rules for identifying the CDR and FR regions are general knowledge of a man skilled in the art and can for example be found in the website (www.bioinf.org.uk/abs/).

In general, there is still a clear need for new and improved ways of inducing regeneration of neural tissue following injury in the adult central nervous system (CNS).

SUMMARY OF THE INVENTION

The invention is directed to a new monoclonal human antibody with superior properties in modulating NogoA activity in in vitro and in vivo experiments and with a positive influence on the neuronal regeneration following injury in the adult central nervous system (CNS). The invention therefore provides new binding molecules to the NogoA protein or fragments thereof.

In one embodiment, the invention therefore provides an isolated molecule comprising at least one antigen binding site which specifically binds to the human NogoA polypeptide (SEQ ID NO: 2) or human NiG (SEQ ID NO: 3), said antigen binding site comprising:
  in sequence the hypervariable regions CDR-H1, CDR-H2, and CDR-H3, wherein each of the hypervariable regions is at least 90% identical to hypervariable regions CDR-H1-6A3 (SEQ ID NO: 8), CDR-H2-6A3 (SEQ ID NO: 9) and CDR-H3-6A3 (SEQ ID NO: 10), respectively; and
  in sequence the hyperyariable regions CDR-L1, CDR-L2, and CDR-L3, wherein each of the hypervariable regions are at least 90% identical to hypervariable regions CDR-Li-6A3 (SEQ ID NO: 11), CDR-L2-6A3 (SEQ ID NO: 12) and CDR-L3-6A3 (SEQ ID NO: 13), respectively.

In a further embodiment, the antigen binding site of said isolated molecule of the invention comprises:
  in sequence the hypervariable regions CDR-H1-6A3 (SEQ ID NO: 8), CDR-H2-6A3 (SEQ ID NO: 9) and CDR-H3-6A3 (SEQ ID NO: 10); and in sequence the hypervariable regions CDR-L1-6A3 (SEQ ID NO: 11), CDR-L2-6A3 (SEQ ID NO: 12) and CDR-L3-6A3 (SEQ ID NO: 13).

In yet another embodiment, the invention provides for a binding molecule which comprises:
- at least one immunoglobulin heavy chain or fragment thereof which comprises (i) a variable domain comprising in sequence the hypervariable regions regions CDR-Hi-6A3 (SEQ ID NO: 8), CDR-H2-6A3 (SEQ ID NO: 9) and CDR-H3-6A3 (SEQ ID NO: 10) and (ii) the constant part or fragment thereof of a human heavy chain; and
- at least one immunoglobulin light chain or fragment thereof which comprises (i) a variable domain comprising in sequence the hypervariable regions CDR-L1-6A3 (SEQ ID NO: 11), CDR-L2-6A3 (SEQ ID NO: 12) and CDR-L3-6A3 (SEQ ID NO: 13) and (ii) the constant part or fragment thereof of a human light chain.

In another embodiment, the binding molecule according to the invention has a dissociation constant <1000 nM.

In an alternative embodiment of the binding molecule of the invention, the constant part or fragment thereof of the human heavy chain is of the γ4 type and the constant part or fragment thereof of the human light chain is of the κ type.

In a further embodiment, the binding molecule according to the invention is a human or chimeric or humanized monoclonal antibody.

In yet another embodiment, the binding molecule according to the invention comprises one or more polypeptide sequences selected from the group consisting of SEQ ID NO: 4 (IgG1 heavy), SEQ ID NO: 5 (IgG1 light), SEQ ID NO: 24 (IgG4 heavy) and SEQ ID NO: 25 (IgG4 light).

In addition, the invention also provides for an isolated polynucleotide comprising a nucleic acid sequence encoding a binding molecule according to the invention.

In certain embodiments, said isolated polynucleotide of the invention comprises either:
- at least one of the polynucleotide sequences selected from the group consisting of SEQ ID NO: 14, SEQ ID NO: 15 and SEQ ID NO: 16; or
- at least one of the polynucleotide sequences selected from the group consisting of SEQ ID NO: 17, SEQ ID NO: 18 and SEQ ID NO: 19.

In preferred embodiments, said polynucleotide of the invention comprises:
- a polynucleotide sequence comprising in sequence SEQ ID NO: 14, SEQ ID NO: 15 and SEQ ID NO: 16; and
- a polynucleotide sequence comprising in sequence SEQ ID NO: 17, SEQ ID NO: 18 and SEQ ID NO: 19.

In yet another preferred embodiment, said polynucleotide of the invention comprises:
- the polynucleotide sequence of SEQ ID NO: 6 and/or the polynucleotide sequence of SEQ ID NO: 7, or,
- the polynucleotide sequence of SEQ ID NO: 26 and/or the polynucleotide sequence of in SEQ ID NO: 28.

Additionally, the present invention also provides an expression vector comprising a polynucleotide according to the invention as defined above.

Furthermore, the invention provides an expression system comprising the expression vector as defined above, wherein said expression system or part thereof is capable of producing a polypeptide of the invention as defined above, when said expression system or part thereof is present in a compatible host cell.

In addition, the present invention also provides an isolated host cell which comprises the vector as defined above.

In addition, the present invention also provides an isolated composition comprising the binding molecule according to the invention and a carrier.

In addition, the present invention also provides an isolated composition comprising the polynucleotide according to the invention, and a carrier.

In addition, the present invention also provides an isolated composition comprising the expression vector of according to the invention, or a host cell according to the invention.

The invention further provides for a method of administering a binding molecule according to the invention to a person in need of treatment of a disease of the peripheral (PNS) and/or central (CNS) nervous system.

The invention also provides a pharmaceutical composition comprising a binding molecule according to the invention, a polynucleotide according to invention, an expression vector or expression system according to the invention, respectively, or a host cell according to the invention, in association with at least one pharmaceutically acceptable carrier or diluent. In certain embodiment, said pharmaceutical composition is a slow release composition.

The invention further provides for a method of treatment of a disease of the peripheral (PNS) and/or central (CNS) nervous system comprising administering to a subject in need of such treatment an effective amount of a binding molecule according to the invention, a polynucleotide according to the invention, an expression vector or system according to the invention, respectively, or a host cell according to the invention. In a preferred embodiment, the disease is a neurodegenerative disease chosen from the group consisting of Alzheimer disease, Parkinson disease, Amyotrophic lateral sclerosis (ALS), Lewy like pathologies or other dementia in general, diseases following cranial, cerebral or spinal trauma, stroke and a demyeliating disease. In a further preferred embodiment, the demyelinating disease is chosen from the group consisting of multiple sclerosis, monophasic demyelination, encephalomyelitis, multifocal leukoencephalopathy, panencephalitis, Marchiafava-Bignami disease, pontine myelmolysis, adrenoleukodystrophy, Pelizaeus-Merzbacher disease, Spongy degeneration, Alexander's disease, Canavan's disease, metachromatic leukodystrophy and Krabbe's disease.

Alternatively, the disease is a degenerative ocular disorder which may directly or indirectly involve the degeneration of retinal or corneal cells. In a preferred embodiment, the degenerative ocular disorder is chosen from the group consisting of ischemic retinopathies, anterior ischemic optic neuropathy, optic neuritis, age-related macular degeneration, diabetic retinopathy, cystoid macular edema (CME), retinitis pigmentosa, Stargardt's disease, Best's vitelliform retinal degeneration, Leber's congenital amaurosis and other hereditary retinal degenerations, pathologic myopia, retinopathy of prematurity, and Leber's hereditary optic neuropathy, the after effects of corneal transplantation or of refractive corneal surgery, and herpes keratitis.

Alternatively, the disease is a , psychiatric condition. Preferably, said psychiatric condition is selected from the group consisting of schizophrenia and depression.

In the methods of treatment as indicated above, the administration is preferably performed intracranially or intrathecally.

In addition, the invention also provides for a method for producing the binding molecule according to the invention, comprising expressing the polynucleotide according to the invention in an expression vector or system according to the invention, by means of recombinant DNA technology or by means of chemical synthesis.

Furthermore, the invention provides a method of administering the pharmaceutical composition according to the invention locally at the site of an injury.

Finally, the invention also provides for a method comprising administering one or more of the following products selected from the group consisting of: a binding molecule according to the invention, a polynucleotide according to the invention, an expression vector or system according to the invention, a host cell according to the invention, as a combined preparation for simultaneous, separate or sequentially use in the treatment of a disease of the peripheral (PNS) and/or central (CNS) nervous system.

The invention further provides a method for producing a binding molecule of the invention and a polynucleotide, an expression vector, by means of recombinant DNA technology or by means of chemical synthesis encoding such a binding molecule.

The present invention also provides a pharmaceutical composition comprising a binding molecule, a polynucleotide, an expression vector or system or a host cell according to the present invention in association with at least one pharmaceutically acceptable carrier or diluent. It also provides products containing said binding molecule, polynucleotide, expression vector or system or said host cell, or a pharmacologically acceptable derivative thereof, as a combined preparation for simultaneous, separate or sequentially use in the treatment of a disease of the peripheral (PNS) and/or central (CNS) nervous system.

A method of treatment of a disease of the peripheral (PNS) and/or central (CNS) nervous system comprising administering to a subject in need of such treatment an effective amount of a binding molecule, a polynucleotide, an expression vector or system or a host cell of the present invention is also envisaged.

The present invention further indicates in the examples that the pharmacological compositions and the products may be used for slow release of the binding molecule and/or for local deposition of the binding molecule at the site of injury.

BRIEF DESCRIPTION OF THE DRAWINGS

FIG. 1 Nucleotide (SEQ ID NO 7) and amino acid (SEQ ID NO 5) encoding the variable regions of the light chain of the 6A3-IgG1 antibody. The underlined section indicates the leader peptide (SED ID NO 22) and the nucleotide sequence encoding the same (SEQ ID NO 23).

FIG. 2 Nucleotide (SEQ ID NO 6) and amino acid (SEQ ID NO 4) sequence encoding the variable regions of the heavy chain of the 6A3-IgG1 antibody. The underlined section indicates the peptide (SEQ ID NO 20) and the nucleotide sequence encoding the same (SEQ ID NO 21).

FIG. 3 Coding regions of the light (SEQ ID NO 28; top) and the heavy (SEQ ID NO 26; bottom) variable part of 6A3-Ig4.

FIG. 4 Amino acids sequences of the heavy (SEQ ID NO 24; bottom) and the light (SEQ ID NO 25, top) chain of 6A3-Ig4 variable and constant part. The leader peptide of the light (SEQ ID NO 31) and heavy (SEQ ID NO 30) chain are indicated in italics.

FIG. 5 Top: 6A3-IgG1 antibody light chain amino acid (SEQ ID NO 5) with leader (SEQ ID NO 22) and CDR-L1 (SEQ ID NO 11), CDR-L2 (SEQ ID NO 12) and CDR-L3 (SEQ ID NO 13) sequences. Bottom: 6A3-IgG1 antibody heavy chain amino acid (SEQ ID NO 4) with leader (SEQ ID NO 20) and CDR-H1 (SEQ ID NO 8), CDR-H2 (SEQ ID NO 9) and CDR-H2 (SEQ ID NO 10) sequences.

FIG. 8

FIG. 8a: Immunofluorescent staining of MO3.13 cells.

FIG. 8b: Immunofluorescent staining of HOG-cells. Immunofluorescent staining of permeabilized MO3.13 cells and HOG cells with the 6A3-IgG4 and the Alexa-Fluor 488-labeled anti human secondary antibody resulted in very bright staining of the cells (FIGS. 8a and 8b, left part), whereas virtually no signal was detected with the secondary antibody only (right part).

FIG. 11 6A3 antibody treatment in monkey SCI model improves the rate and degree of functional recovery irrespective of lesion size.

DETAILED DESCRIPTION OF THE INVENTION

Figure 6:
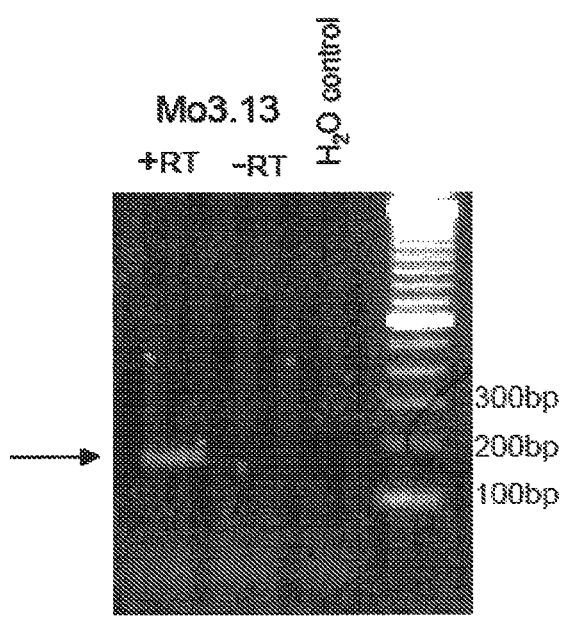
FIG. 6 RT-PCR using the MO3.13 RNA as template and Nogo-A specific primers resulted in a distinct DNA fragment of around 200 bp.

In the search for new and improved ways to provide neuronal regeneration following injury in the adult central nervous system (CNS), it has now surprisingly been found that a novel monoclonal human antibody 6A3 that was generated in the HuMab-mouse™ by Medarex Inc, genetically reconstituted mice wherein human immunoglobulin genes replace their murine counterparts, has superior properties in modulating NogoA activity in in vitro and in vivo experiments. 6A3 was raised against human NiG, is of the IgG isotype and has better properties than the NogoA antibodies described in the prior art. It is now possible to construct other NogoA binding molecules having the same hypervariable regions as said 6A3 antibody, creating new antibodies having the advantageous properties of 6A3. Derivates of the 6A3-Ab, 6A3-IgG4 and 6A3-Fab recognize the human NiG with a high affinity of 0.14nM and 1.1 nM, respectively. Furthermore, the antibodies of the present invention show a high stability and extended in vitro and in vivo high half-life and retention. Finally the binding molecules and antibodies of the invention display a slow release from the site of introduction, making local depositions of the binding molecules at the site of injury possible. High cerebrospinal (CSF) concentrations of the 6A3 antibody in spinal cord injury animals and patients by continuous infusion have been detected. This surprisingly high 6A3-Ab retention and residency in, for instance, the cerebrospinal fluid makes it possible to use bolus injections (of for instance 1-3 times per week, although even longer intervals of once per 2, 3 or 4 weeks may be feasible) instead of constantly infusing the antibody into the cerebrospinal fluid. Repeated intrathecal bolus injections may be used. In a preferred embodiment, the administration is done through intrathecal ad ministration, using a n externalized catheter connected to a portable pump. In a further preferred embodiment, intrathecal bolus injection is used. The experimental section further illustrates the advantageous properties of the binding molecules of the invention.

Accordingly, the invention provides binding molecules to NogoA or NiG (hereinafter referred to as "the Binding Molecules of the invention" or simply "Binding Molecules"). Preferably, the Binding Molecules of the invention bind human NogoA protein (SEQ ID NO: 2, encoded by SEQ ID NO: 1) or human NiG protein (which is the most potent neurite outgrowth inhibitory fragment of NogoA and starts at amino acid No. 186 and ends at amino acid No. 1004 of human NogoA, =SEQ ID NO: 3) preferably with a dissociation constant (Kd)<1000 nM, or with a Kd up to and including 100 nM, more preferably with a Kd<100 nM, or with a Kd up to and including 100 nM, most preferably with a Kd<10 nM, or with a Kd up to and including 10 nM. The binding reaction may be shown by standard methods (including both qualitative and quantitative assays) including, for example, Western blotting, immunoprecipitation and biosensor affinity methods (cf. Example 4). In addition, the binding of the Binding Molecules of the invention to human NogoA and human NiG, and the efficacy of these binding molecules in functional assays may be shown in a neurite outgrowth assay, e.g. as described below.

Thus, in a further preferred embodiment the Binding Molecules of the present invention (at a concentration of 100 µg/ml, preferably 10 µg/ml, more preferably at 1.0 µg/ml even more preferably at 0.1 µg/ml) enhance the number of neurites of rat cerebellar granule cells on a substrate of monkey brain protein extract by at least 20%, preferably 50%, most preferably 80%, when compared to the number of neurites of rat cerebellar granule cells which are treated with a control antibody that does not bind to the human NogoA polypeptide or human NiG polypeptide (i.e. that has a dissociation constant >1000 nM).

In another embodiment the invention relates to an isolated molecule comprising at least one antigen binding site which specifically binds to the human NogoA polypeptide (SEQ ID NO: 2) or human NiG polypeptide (SEQ ID NO: 3), comprises at least one antigen binding site, said antigen binding site comprising:
- at least one of the hypervariable regions CDR-H1, CDR-H2, and CDR-H3, where each of the hypervariable regions is at least 90% identical the hypervariable regions of CDR-H1-6A3 (SEQ ID NO: 8), CDR-H2-6A3 (SEQ ID NO: 9) and CDR-H3-6A3 (SEQ ID NO: 10), respectively; and
- at least one of the hypervariable regions CDR-L1, CDR-L2, and CDR-L3, where each of the hypervariable regions is at least 90% identical to the hypervariable regions of CDR-L1-6A3 (SEQ ID NO: 11), CDR-L2-6A3 (SEQ ID NO: 12) and CDR-L3-6A3 (SEQ ID NO: 13), respectively.

Specific recognition of the human NogA or MG is guaranteed when CDR-H1, CDR- H2 and CDR-H3 or CDR-L1, CDR- L2 and CDR-L3 are present in the binding molecule of the present invention. Nevertheless, it is known by the skilled person that even the presence of only one CDR-domain in the binding molecule may be enough to ensure specific binding to the recognized molecule. The phrase "at least one of the hypervariable regions" means 1, or 2 or 3 hypervariable regions. The phrase "at least 90% identity" means more than 90% identity, preferably more than 91%, 92%, 93%; 94%, 95%, 96%, 97%, 98%, 99% identity. The percent identity between two amino acid sequences can be determined using a computer algorithm which analyzes the relative identity of two or more amino acid sequences identity, e.g., Basic Local Alignment Search Tool, (BLAST) on the National Institutes of Health web site, Altschul et al. 1994, Nature Genetics, 6:119-129, Altschul et al. 1990, 3. Mol. Biol.215:403-410, Altkhul et al. 1997,Nucleic Acids Research, 25:1389-1402, Karlin and Altschul, 1990 PNAS, 87:2264-68, Karlin and Altschul, 1993 PNAS, 90:5873-68.

The present invention relates to an isolated molecule comprising at least one antigen binding site which specifically binds to the human NogoA polypeptide (SEQ ID NO: 2) or human NiG (SEQ ID NO: 3) with a dissociation constant <1000nM, said antigen binding site comprising:
- at least the hypervariable regions CDR-H1, CDR-H2, and CDR-H3, wherein each of the hypervariable regions is at least 90% identical to hypervariable regions CDR-H1-6A3 (SEQ ID NO: 8), CDR-H2-6A3 (SEQ ID NO: 9) and CDR-H3-6A3 (SEQ ID NO: 10), respectively; and
- at least the hypervariable regions CDR-L1, CDR-L2, and CDR-L3, wherein each of the hypervariable regions are at least 90% identical to hypervariable regions CDR-L1-6A3 (SEQ ID NO: 11), CDR-L2-6A3 (SEQ ID NO: 12) and CDR-L3-6A3 (SEQ ID NO: 13), respectively.

The phrase "antigen binding site comprising in sequence the hypervariable regions" encompasses an antigen binding site in which the hypervariable regions are not contiguous with each other; preferably said antibody regions are interspersed with antibody framework regions, or with sequences that are non-antibody framework sequences, preferably human antibody framework regions. According to the present invention the binding molecule may also comprise at least one antigen binding site, said antigen binding site comprising either:
- in sequence the hypervariable regions CDR-H1-6A3 (SEQ ID NO: 8), CDR-H2-6A3 (SEQ ID NO: 9) and CDR-H3-6A3 (SEQ ID NO: 10); or
- in sequence the hypervariable regions CDR-L1-6A3 (SEQ ID NO: 11), CDR-L2-6A3 (SEQ ID NO: 12) and CDR-L3-6A3 (SEQ ID NO: 13); or
- direct equivalents thereof which are at least 90% identical to the sequence of said hypervariable regions. The phrase "at least 90% identity" means more than 90% identity, preferably more than 91%, 92%, 93%; 94%, 95%, 96%, 97%, 98%, 99% Identity.

According to the present invention the binding molecule may also comprise:
- a first antigen binding site comprising in sequence the hypervariable regions CDR-Hi-6A3 (SEQ ID NO: 8), CDR-H2-6A3 (SEQ ID NO: 9) and CDR-H3-6A3 (SEQ ID NO: 10); and
- a second antigen binding site comprising in sequence the hypervariable regions CDR-L1-6A3 (SEQ ID NO: 11), CDR-L2-6A3 (SEQ ID NO: 12) and CDR-L3-6A3 (SEQ ID NO: 13); or
- direct equivalents thereof which are at least 90% identical to the sequence of said hypervariable regions. At least 90% identity means more than 90% identity, preferably more than 91%, 92%, 93%; 94%, 95%, 96%, 97%, 98%, 99%.

According to the present invention the binding molecule may also comprise:
- at least one immunoglobulin heavy chain or fragment thereof which comprises (i) a variable domain comprising in sequence the hypervariable regions CDR-H1-6A3 (SEQ ID NO: 8), CDR-H2-6A3 (SEQ ID NO: 9) and CDR-H3-6A3 (SEQ ID NO: 10) and (ii) the constant part or fragment thereof of a human heavy chain; and
- at least one immunoglobulin light chain or fragment thereof which comprises (i) a variable domain comprising in sequence the hypervariable regions CDR-L1-6A3 (SEQ ID NO: 11), CDR-L2-6A3 (SEQ ID NO: 12) and CDR-L3-6A3 (SEQ ID NO: 13) and (ii) the constant part or fragment thereof of a human light chain; or direct equivalents thereof which are at least 90% identical to the sequence of said hypervariable regions. At least 90% identity means more than 90% identity, preferably more than 91%, 92%, 93%; 94%, 95%, 96%, 97%, 98%, 99% identity.

In the binding molecule of the present invention the constant part or fragment thereof of the human heavy chain may be of the gamma (γ) type, preferably the gamma 4 (γ4) type and the constant part or fragment thereof of the human light chain may of the lambda (λ) or preferably the kappa (κ) type. In addition, the binding molecule of the present invention may be a human, partly human or chimeric or humanized monoclonal antibody.

According to the present invention, the binding molecule may comprise one or more polypeptide sequences as shown in any of SEQ ID NO: 4 (IgG1 heavy), SEQ ID NO:5 (IgG1 light), SEQ ID NO:24 (IgG4 heavy) and SEQ ID NO:25 (IgG4 light).

In a further preferred embodiment the Binding Molecule of the present invention comprises at least one antigen binding site, said antigen binding site comprising in sequence, the hypervariable regions CDR-H1-6A3, CDR-H2-6A3 and CDR-H3-6A3; said CDR-H1-6A3 having the amino acid sequence SEQ ID NO: 8, said CDR-H2-6A3 having the amino acid sequence SEQ ID NO: 9, and said CDR-H3-6A3 having the amino acid sequence SEQ ID NO: 10; and direct equivalents thereof which are at least 90% identical to the sequence of said hypervariable regions. At least 90% identity means more than 90% identity, preferably more than 91%, 92%, 93%; 94%, 95%, 96%, 97%, 98%, 99% identity.

In a further aspect of the invention, the Binding Molecule of the invention comprises at least:

a) a first domain comprising in sequence the hypervariable regions CDR-H1-6A3, CDR-H2-6A3 and CDR-H3-6A3; said CDR-H1-6A3 having the amino acid sequence of SEQ ID NO: 8, said CDR-H2-6A3 having the amino acid sequence of SEQ ID NO: 9, and said CDR-H3-6A3 having the amino acid sequence SEQ ID NO: 10; and b) a second domain comprising in sequence the hypervariable regions CDR-L1-6A3, CDR-L2-6A3 and CDR-L3-6A3, said CDR-L1-6A3 having the amino acid sequence of SEQ ID NO: 11, said CDR-L2-6A3 having the amino acid sequence of SEQ ID NO: 12, and said CDR-L3-6A3 having the amino acid sequence of SEQ ID NO: 13; or c) direct equivalents thereof which are at least 90% identical to the sequence of said hypervariable regions. At least 90% identity means more than 90% identity, preferably more than 91%, 92%, 93%; 94%, 95%, 96%, 97%, 98%, 99% identity.

Moreover, the invention also provides the following Binding Molecule of the invention, which comprises at least one antigen binding site comprising:

a) either the variable region of the heavy chain of 6A3 (SEQ ID NO: 4); or b) the variable region of the light chain of 6A3 (SEQ ID NO: 5), or direct equivalents thereof which are at least 90% identical to the sequence of said hypervariable regions.

When the antigen binding site comprises both the first and second domains, these may be located on the same polypeptide molecule or, preferably, each domain may be on a different chain, the first domain being part of an immunoglobulin heavy chain or fragment thereof and the second domain being part of an immunoglobulin light chain or fragment thereof.

Examples of Binding Molecules of the invention include antibodies as produced by B-cells or hybridomas and human or chimeric or humanized antibodies or any fragment thereof, e.g. F(ab')2; and Fab fragments, as well as single chain or single domain antibodies, as described in US patent publication US20070065440A1.

As used herein, a "single domain antibody" is a variable domain which can specifically bind an epitope or an antigen or a ligand independently of another Variable binding domain which binds that epitope, antigen or ligand. A single domain antibody can be present in a homo-or heteromultimer with other VH or VL domains where the other domains are not required for antigen binding by the single domain antibody, i.e., where the single domain antibody binds antigen independently of the additional VH or VL domains. In a preferred embodiment, a single domain antibody, comprises an isolated VH single domain or an isolated VL single domain. Techniques for obtaining a single domain antibody with at least some of the binding specificity of the intact antibody from which they are derived are known in the art. For instance, Ward, et al., in "Binding Activities of a Repertoire of Single Immunoglobulin Variable Domains Secreted from *Escherichia coli*," Nature 341:644-646, disclose a method for screening to obtain an antibody heavy chain variable region (VH single domain antibody) with sufficient affinity for its target epitope to bind thereto in isolate form. A single chain antibody consists of the variable domains/regions of an antibody heavy and light chains covalently bound by a peptide linker usually consisting of from 10 to 30 amino acids, preferably from 15 to 25 amino acids. Preferred methods include the use of polypeptide linkers, as described, for example, in connection with scFv molecules (Bird et al., (1988) Science 242: 423-426). Therefore, such a structure does not include the constant part of the heavy and light chains and it is believed that the small peptide spacer should be less antigenic than a whole constant part. By "chimeric antibody" is meant an antibody in which the constant regions of the heavy or light antibody chains or both, or both, have an origin from a first species, while the variable regions of both heavy and light chains have an origin of a second species. Preferably, a "chimeric antibody" is an antibody in which the constant regions of the heavy or light chains, or both, are of human origin while the variable domains of both heavy and light chains are of non- human (e.g. murine, monkey, rat, pig, mouse, chicken, avian,) origin. By "humanized antibody" is meant an antibody in which the hypervariable regions (CDRs) are of non-human (e.g. murine) origin, while all or substantially all the other parts of the immunoglobulin e.g. the constant regions and the highly conserved parts of the variable domains, i.e. the framework regions, are of human origin. A humanized antibody may however retain a few amino acids of the murine sequence in the parts of the framework regions adjacent to the hypervariable regions.

Hypervariable regions may be associated with any kind of framework regions, preferably of murine or human origin. Suitable framework regions are described in "Sequences of proteins of immunological interest", Kabat E. A. et al, US department of health and human services, Public health service, National Institute of Health. Preferably the constant part of a human heavy chain of the Binding Molecules may be of the the IgG type, more preferably the IgG4 type, including subtypes, preferably the constant part of a human light chain may be of the lambda (λ) or kappa (κ) type, more preferably of the kappa (κ) type.

Monoclonal antibodies raised against a protein naturally found in all humans may be developed in a non-human system, e. g., in mice. As a direct consequence of this, a xenogenic antibody as produced by a hybridoma, when administered to humans, elicits an undesirable immune response, which is predominantly mediated by the constant part of the xenogenic immunoglobulin. This clearly limits the use of such antibodies as they cannot be administered over a prolonged period of time. Therefore it is particularly preferred to use single chain, single domain, chimeric or humanized antibodies which are not likely to elicit a substantial allogenic response when administered to humans.

In view of the foregoing, the Binding Molecule of the invention may also be selected from a chimeric antibody, which comprises at least:

a) one immunoglobulin heavy chain or fragment thereof which comprises (i) a variable domain comprising in sequence the hypervariable regions CDR-H1-6A3, CDR-H2-6A3 and CDR-H3-6A3 and (ii) the constant part or fragment thereof of a human heavy chain; said CDR-H1-6A3 having the amino acid sequence (SEQ ID NO: 8), said CDR-H2-6A3 having the amino acid sequence (SEQ ID NO: 9), and said CDR-H3-6A3 having the amino acid sequence (SEQ ID NO: 10), and b) one immunoglobulin light chain or fragment thereof which comprises (i) a variable domain comprising in sequence the hypervariable regions CDR-L1-6A3, CDR-L2-6A3 and CDR-L3-6A3 and (ii) the constant part or fragment thereof of a human light chain; said CDR-L1-6A3 having the amino acid sequence (SEQ ID NO: 11), said CDR-L2-6A3 having the amino acid sequence (SEQ ID NO: 12), and said CDR-L3-6A3 having the amino acid sequence (SEQ ID NO: 13); or direct equivalents thereof which comprise regions that are at least 90% identical to the sequence of said hypervariable regions.

Alternatively, a Binding Molecule of the invention may be selected from a single chain binding molecule which comprises an antigen binding site comprising:

a) a first domain comprising in sequence the hypervariable CDR-H1-6A3, CDR-H2-6A3 and CDR-H3-6A3; said CDR-H1-6A3 having the amino acid sequence (SEQ ID NO: 8), said CDR-H2-6A3 having the amino acid sequence (SEQ ID NO: 9), and said CDR-H3-6A3 having the amino acid sequence (SEQ ID NO: 10); and b) a second domain comprising in sequence the hypervariable CDR-L1-6A3, CDR-L2-6A3 and CDR-L3-6A3; said CDR-L1-6A3 having the amino acid sequence (SEQ ID NO: 11), said CDR-L2-6A3 having the amino acid sequence (SEQ ID NO: 12), and said CDR-L3-6A3 having the amino acid sequence (SEQ ID NO: 13); and c) a peptide linker which is bound either to the N- terminal extremity of the first domain and to the C-terminal extremity of the second domain or to the C-terminal extremity of the first domain and to the N-terminal extremity of second domain; or direct equivalents thereof which are at least 90% identical to the sequence of said hypervariable regions.

As it is well known, minor changes in an amino acid sequence such as deletion, addition or substitution of one or several amino acids may lead to an allelic form of the original protein which has substantially identical properties. Thus, by the term "direct equivalents thereof" is meant either any hypervariable region, any antigen binding site, any antibody chain or fragment thereof, or any single domain Binding Molecule of the invention (molecule 6A3)

(i) in which each of the hypervariable regions CDR-H1, CDR-H2, and CDR-H3 of the Binding Molecule is at least 90% identical, more preferably at least 91, 92, 93, 94, 95, 96, 97, 98, 99% identical to the equivalent hypervariable regions of CDR-H1-6A3 (SEQ ID NO: 8), CDR-H2-6A3 (SEQ ID NO: 9) and CDR-H3-6A3 (SEQ ID NO: 10), whereas CDR-H1 is equivalent to CDR-H1-6A3, CDR-H2 is equivalent to CDR-H2-6A3, CDR-H3 is equivalent to CDR-H3-6A3; and (ii) which is capable of binding to the human NogoA or human NiG, preferably with a dissociation constant (Kd) <1000nM, more preferably with a Kd <100 nM, most preferably with a Kd <10 nM, or any binding molecule of the invention having at least one, preferably two domains per binding site (molecule 6A3)

(iii) in which each of the hypervariable regions CDR-H1, CDR-H2, CDR-H3, CDR-L1, CDR-L2 and CDR-L3 is at least 90% identical, more preferably at least 91, 92, 93, 94, 95, 96, 97, 98, 99% identical to the equivalent hypervariable regions of CDR-H1-6A3 (SEQ ID NO: 8), CDR-H2-6A3 (SEQ ID NO: 9), CDR-H3-6A3 (SEQ ID NO: 10), CDR-L1-6A3 (SEQ ID NO: 11), CDR-L2-6A3 (SEQ ID NO: 12), and CDR-L3-6A3 (SEQ ID NO: 13), whereas CDR-H1 is equivalent to CDR-H1-6A3, CDR-H2 is equivalent to CDR-H2-6A3, CDR-H3 is equivalent to CDR-H3-6A3, CDR-L1 is equivalent to CDR-L1-6A3, CDR-L2 is equivalent to CDR-L2-6A3, CDR-L3 is equivalent to CDR-L3-6A3; and (iv) which is capable of binding the human NogoA or human NiG, preferably with a dissociation constant (Kd) <1000nM, more preferably with a Kd<100 nM, most preferably with a Kd <10 nM.

Thus further embodiments of the inventions are for example a Binding Molecule which is capable of binding to the human NogoA or human NiG with a dissociation constant <1000 nM and comprises at least one antigen binding site, said antigen binding site comprising either in sequence the hypervariable regions CDR-H1, CDR-H2, and CDR-H3, of which each of the hypervariable regions is at least 90%, preferably 91, 92, 93, 94, 95, 96, 97, 98, 99% identical to hypervariable regions CDR-H1-6A3 (SEQ ID NO: 8), CDR-H2-6A3 (SEQ ID NO: 9) and CDR-H3-6A3 (SEQ ID NO: 10), respectively; and/ or in sequence the hypervariable regions CDR-L1, CDR-L2, and CDR-L3, of which each of the hypervariable regions is at least 90%, preferably 91, 92, 93, 94, 95, 96, 97, 98, 99% identical to hypervariable regions CDR-L1-6A3 (SEQ ID NO: 11), CDR-L2-6A3 (SEQ ID NO: 12) and CDR-L3-6A3 (SEQ ID NO: 13), respectively.

Furthermore, a Binding Molecule as described herein is capable of binding the human NogoA or human NiG with a dissociation constant <1000 nM and comprises:

a first antigen binding site comprising in sequence the hypervariable regions CDR-H1, CDR-H2, and CDR-H3, of which each of the hypervariable regions is at least 90%, preferably 91, 92, 93, 94, 95, 96, 97, 98, 99% identical to hypervariable regions CDR-H1-6A3 (SEQ ID NO: 8), CDR-H2-6A3(SEQ ID NO: 9) and CDR-H3-6A3 (SEQ ID NO: 10), respectively; and a second antigen binding site comprising in sequence the hypervariable regions CDR-L1, CDR-L2, and CDR-L3, of which each of the hypervariable regions is at least 90%, preferably 91, 92, 93, 94, 95, 96, 97, 98, 99% identical to hypervariable regions CDR-L1-6A3 (SEQ ID NO: 11), CDR-L2-6A3 (SEQ ID NO: 12) and CDR-L3-6A3 (SEQ ID NO: 13), respectively.

This dissociation constant may be conveniently tested in various assays including, for example, the biosensor affinity method (BIAcore) (see above). In addition, the binding and functional affect of the Binding Molecules may be shown in a bioassay, e.g. as described below.

The constant part of a human heavy chain may be of the γ1; γ2; γ3; γ4; α1; α2; δ or ε type, preferably of the γ type, more preferably of the γ4; type, whereas the constant part of a human light chain may be of the λ or κ type (which includes the λ1; λ2; λ3; and λ4 subtypes) but is preferably of the κ type. The amino acid sequence of all these constant parts are given in Kabat et al (Supra).

Conjugates of the binding molecules of the invention, e. g. enzyme or toxin or radioisotope conjugates, are also included within the scope of the invention. In another aspect, a NogoA or NiG binding molecule containing composition is stabilized in vivo by linkage or association with a (non-polypeptide) polymeric stabilizing moiety, such as glycosylation, as obtainable by in vitro or in vivo processes. Examples of this type of stabilization are described, for example, in WO99/64460 (Chapman et al.) and EP1,160,255 (King et al.), each of which is incorporated herein by reference. Specifically, these references describe the use of synthetic or naturally-occurring polymer molecules, such as polyalkylene, polyalkenylenes, polyoxyalkylenes or polysaccharides, to increase the in vivo half-life of immunoglobulin polypeptides. A typical example of a stabilizing moiety is polyethylene glycol, or PEG, a polyalkylene. The process of linking PEG to an immunoglobulin polypeptide is described in these references and is referred to herein as "PEGylation." As described therein, an NogoA or NiG binding molecule can be PEGylated randomly, as by attachment of PEG to lysine or other amino acids on the surface of the NogoA or NiG binding molecule, or site-specifically, e.g., through PEG attachment to an artificially introduced surface cysteine residue. Depending upon the NogoA or NiG binding molecule, it may be preferred to use a non-random method of polymer attachment, because random attachment, by attaching in or near the antigen-binding site or sites on the molecule often alters the affinity or specificity of the molecule for its target antigen.

It is preferred that the addition of PEG or another polymer does not interfere with the antigen-binding affinity or specificity of the antibody NogoA or NiG binding molecule. By "does not interfere with the antigen-binding affinity or specificity" is meant that the PEG-linked NogoA or NiG binding molecule has an 1050 or ND50 which is no more than 10% greater than the 1050 or ND50, respectively, of a non-PEG-linked NogoA or NiG binding molecule having the same antibody single variable domain. In the alternative, the phrase "does not interfere with the antigen-binding affinity or specificity" means that the PEG-linked form of NogoA or NiG binding molecule retains at least 90% of the antigen binding activity of the non-PEGylated form of the polypeptide. The PEG or other polymer useful to increase the in vivo half-life is generally about 5,000 to 50,000 Daltons in size, e.g., about 5,000 kD-10,000 kD, 5,000 kD-15,000 kD, 5,000 kD-20,000 kD, 5,000-25,000 kD, 5,000-30,000 kD, 5,000 kD-35,000 kD, 5,000 kD-40,000 kD, or about 5,000 kD-45,000. The choice of polymer size depends upon the intended use of the complex. For example, where it is desired to penetrate solid tissue, e.g., a tumor, it is advantageous use a smaller polymer, on the order or about 5,000 kD. Where, instead, it is desired to maintain the complex in circulation, larger polymers, e.g., 25,000 kD to 40,000 kD or more can be used. The pharmaceutical compositions of the invention may include a "therapeutically effective amount" or a "prophylactically effective amount" of a NogoA or Nig binding molecule of the invention. A "therapeutically effective amount" refers to an amount effective, at dosages and for periods of time necessary, to achieve the desired therapeutic result. A therapeutically effective amount of the NogoA or Nig binding molecule of the invention may vary according to factors such as the disease state, age, sex, and weight of the individual, and the ability of the NogoA or Nig binding molecule of the invention to elicit a desired response in the individual. A therapeutically effective amount is also one in which any toxic or detrimental effects of the NogoA or Nig binding molecule of the invention are outweighed by the therapeutically beneficial effects. A "prophylactically effective amount" refers to an amount effective, at dosages and for periods of time necessary, to achieve the desired prophylactic result.

As used herein, the phrase "specifically binds" refers to the binding of an antigen by an NogoA or Nig binding molecule of the invention with a dissociation constant (Kd) of 1 μM or lower as measured by surface plasmon resonance analysis using, for example, a BIAcore(r) surface plasmon resonance system and BIAcore(r) kinetic evaluation software.

"Polypeptide", if not otherwise specified herein, includes any peptide or protein comprising amino acids joined to each other by peptide bonds, having an amino acid sequence starting at the N-terminal extremity and ending at the C-terminal extremity. Preferably, the polypeptide of the present invention is a monoclonal antibody, more preferred is a chimeric (also called V-grafted) or humanised (also called CDR-grafted) monoclonal antibody. The humanised (CDR-grafted) monoclonal antibody may or may not include further mutations introduced into the framework (FR) sequences of the acceptor antibody.

A functional derivative of a polypeptide as used herein includes a molecule having a qualitative biological activity in common with a polypeptide to the present invention, i.e. having the ability to bind to the human NogoA or human NiG. A functional derivative includes fragments and peptide analogs of a polypeptide according to the present invention. Fragments comprise regions within the sequence of a polypeptide according to the present invention, e.g. of a specified sequence. The term "derivative" is used to define amino acid sequence variants, and covalent modifications of a polypeptide according to the present invention. e.g. of a specified sequence. The functional derivatives of a polypeptide according to the present invention, e.g. of a specified sequence, e.g. of the hypervariable region of the light and the heavy chain, preferably have at least about 90%, more preferably at least about 91, 92, 93, 94, 95, 96, 97, 98, 99% overall sequence identity with the amino acid sequence of a polypeptide according to the present invention, e.g. of a specified sequence, and substantially retain the ability to bind the human NogoA or human NiG. As used herein, the phrase "variable domain" refers to a polypeptide having a sequence derived from a mammalian germline immunoglobulin V region. A sequence is "derived from a mammalian germline V region" when the sequence is either isolated from a human individual, isolated from a non human animal, such as a rodent such as a mouse, in which the non human animal is capable of generating human immunoglobulins in response to an immunogen, more preferably said non human animal is not able to produce antibodies endogenous to its species, isolated from a library of cloned human antibody gene sequences (or a library of human antibody V region gene sequences), or when a cloned human germline V region sequence was used to generate one or more diversified sequences (by random or targeted mutagenesis) that were then selected for binding to a desired target antigen. At a minimum, a human immunoglobulin variable domain has at least 85% amino acid similarity (including, for example, 87%, 90%, 93%, 95%, 97%, 99% or higher similarity) to a naturally-occurring human immunoglobulin variable domain sequence. Alternatively, or in addition, "variable domain" is an immunoglobulin variable domain that comprises four immunoglobulin variable domain framework regions (FW1-FW4) which are preferably human, as framework regions are set forth by Kabat et al. (1991,). The "variable domain framework regions" encompass a) an amino acid sequence of a framework region, preferably human, and b) a framework region that comprises at least 8 contiguous amino acids of the amino acid sequence of a human framework region. An antibody variable domain can comprise amino acid sequences of FW1-FW4 that are the same as the amino acid sequences of corresponding framework regions encoded by a germline antibody gene segment, preferably human, or it can also comprise a variable domain in which FW1-FW4 sequences collectively contain up to 10 amino acid sequence differences (e.g., up to 1, 2, 3, 4, 5, 6, 7, 8, 9 or 10 amino acid sequence differences) relative to the amino acid sequences of corresponding framework regions encoded by a germline antibody gene segment, preferably human. As used herein, the phrase "universal framework" refers to a single antibody framework sequence corresponding to the regions of an antibody conserved in sequence as defined by Kabat et al. (1991) or corresponding to the human germline immunoglobulin repertoire or structure as defined by Chothia and Lesk, (1987) 3. Mol. Biol. 196:910-917. The invention provides for the use of a single framework, or a set of such frameworks, which has been found to permit the derivation of virtually any binding specificity though variation in the hypervariable regions alone. In one embodiment, the hypervariable regions or CDRs specifically bind NogoA and/or NiG.

The term "covalent modification" includes modifications of a polypeptide according to the present invention, e.g. of a specified sequence; or a fragment thereof with an organic proteinaceous or non-proteinaceous derivatizing agent, fusions to heterologous polypeptide sequences, and post-translational modifications. Covalent modified polypeptides, e.g. of a specified sequence, still have the ability bind to the human NogoA or human NiG by crosslinking. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deaminated under mildly acidic conditions. Other post-translational modifications include hydroxylation of proline and lysine, phosphorylation of hydroxyl groups of seryl, tyrosine or threonyl residues, methylation of the α-amino groups of lysine, arginine, and histidine side chains, see e.g. T. E. Creighton, Proteins: Structure and Molecular Properties, W. H. Freeman & Co., San Francisco, pp. 79-86 (1983). Covalent modifications may include fusion proteins comprising a polypeptide according to the present invention, e.g. of a specified sequence and their amino acid sequence variants, such as immunoadhesins, and N-terminal fusions to heterologous signal sequences.

"Identity" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent identity, and not considering any conservative substitutions as part of the sequence identity. Neither N- or C-terminal extensions nor insertions shall be construed as reducing identity. Methods and computer programs for the alignment are well known, see Altschul et al. supra.

"Amino acid(s)" refer to all naturally occurring L-α-amino acids, e.g. and including D-amino acids. The amino acids are identified by either the well known single-letter or three-letter designations.

The term "amino acid sequence variant" refers to molecules with some differences in their amino acid sequences as compared to a polypeptide according to the present invention, e.g. of a specified sequence. Amino acid sequence variants of a polypeptide according to the present invention, e.g. of a specified sequence, may still have the ability to bind to human NogoA or human NiG. Substitutional variants are those that have at least one amino acid residue removed and a different amino acid inserted in its place at the same position in a polypeptide according to the present invention, e.g. of a specified sequence. These substitutions may be single, where only one amino acid in the molecule has been substituted, or they may be multiple, where two or more amino acids have been substituted in the same molecule. Insertional variants are those with one or more amino acids inserted immediately adjacent to an amino acid at a particular position in a polypeptide according to the present invention, e.g. of a specified sequence. Immediately adjacent to an amino acid means connected to either the α-carboxy or α-amino functional group of the amino acid. Deletional variants are those with one or more amino acids in a polypeptide according to the present invention, e.g. of a specified sequence, removed. Ordinarily, deletional variants will have one or two amino acids deleted in a particular region of the molecule.

A binding molecule of the invention may be produced by recombinant DNA techniques. In general, the nucleic acid molecules and vector constructs required for the performance of the present invention may be constructed and manipulated as set forth in standard laboratory manuals, such as Sambrook et al. (1989) Molecular Cloning: A Laboratory Manual, Cold Spring Harbor, USA. In view of this, one or more DNA molecules encoding the binding molecule must be constructed, placed under appropriate control sequences and transferred into a suitable host organism for expression.

In a very general manner, there are accordingly provided herein, (i) DNA molecules encoding a hypervariable region, an antigen binding site, an antibody chain or fragment thereof, or a single domain Binding Molecule of the present invention; and (ii) the use of the DNA molecules of the invention for the production of a Binding Molecule of the present invention by recombinant means.

The present state of the art is such that the skilled person will be able to synthesize the DNA molecules of the invention given the information provided herein i.e. the amino acid sequences of the hypervariable regions and the DNA sequences coding for them. A method for constructing a variable domain gene is for example described in EP 239 400 and may be briefly summarized as follows: A gene encoding a variable domain of a monoclonal antibody of whatever specificity is cloned. The DNA segments encoding the framework and hypervariable regions are determined and the DNA segments encoding the hypervariable regions are removed so that the DNA segments encoding the framework regions are fused together with suitable restriction sites at the junctions. The restriction sites may be generated at the appropriate positions by mutagenesis of the DNA molecule by standard procedures. Double stranded synthetic CDR cassettes are prepared by DNA synthesis according to the sequences given CDR-H1-6A3, CDR-H2-6A3, CDR-H3-6A3, CDR-L1-6A3, CDR-L2-6A3 above. These cassettes are provided with sticky ends so that they can be ligated at the junctions to the framework by standard protocol for achieving a DNA molecule encoding an immunoglobulin variable domain.

Furthermore, it is not necessary to have access to the mRNA from a producing hybridoma cell line in order to obtain a DNA construct coding for the monoclonal antibodies of the invention. Thus PCT application WO 90/07861 gives full instructions for the production of a monoclonal antibody by recombinant DNA techniques given only written information as to the nucleotide sequence of the gene.

The method comprises the synthesis of a number of oligo-nucleotides, their amplification by the PCR method, and their splicing to give the desired DNA sequence.

Numerous vectors are publicly available, including bacterial plasmids, bacteriophage, artificial chromosomes and episomal vectors. Expression vectors comprising aone or more suitable promoter promoters and/or genes encoding heavy and light chain constant parts are publicly available. Expression vectors usually contain a promoter that is recognized by the host organism and is operably linked to the coding sequence of interest. Such a promoter may be inducible or constitutive. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Thus, once a DNA molecule of the invention is prepared it may be conveniently transferred in an appropriate expression vector.

DNA molecules encoding single chain antibodies may also be prepared by standard methods, for example, as described in WO 88/1649.

In a particular embodiment of the invention, the recombinant means for the production of some of the Binding Molecules of the invention includes first and second DNA constructs as described below:

The first polynucleotide may comprise either:
  at least one of the polynucleotide sequences as shown in SEQ ID NO: 14, SEQ ID NO: 15 and SEQ ID NO: 16; or
  at least one of the polynucleotide sequences as shown in SEQ ID NO: 17, SEQ ID NO: 18 and SEQ ID NO: 19.

Another polynucleotide according to the invention comprises:
  a polynucleotide sequence as shown in SEQ ID NO: 14, SEQ ID NO: 15 and SEQ ID NO: 16; and
  a polynucleotide sequence as shown in SEQ ID NO: 17, SEQ ID NO: 18 and SEQ ID NO: 19.

In another embodiment the polynucleotide comprises:
  a polynucleotide sequence as shown in SEQ ID NO: 6 and/or a polynucleotide sequence as shown in SEQ ID NO: 7, or,
  a polynucleotide sequence as shown in SEQ ID NO: 26 and/or a polynucleotide sequence as shown in SEQ ID NO: 28.

In yet another embodiment the DNA construct encodes a heavy chain or fragment thereof and comprises:
a) a first part which encodes a variable domain comprising alternatively framework and hypervariable regions, said hypervariable regions comprising in sequence DNA-CDR-H1-6A3 (SEQ ID NO: 14), DNA-CDR-H2-6A3 (SEQ ID NO: 15) and DNA-CDR-H3-6A3 (SEQ ID NO: 16); this first part starting with a codon encoding the first amino acid of the variable domain and ending with a codon encoding the last amino acid of the variable domain, and
b) a second part encoding a heavy chain constant part or fragment thereof which starts with a codon encoding the first amino acid of the constant part of the heavy chain and ends with a codon encoding the last amino acid of the constant part or fragment thereof, followed by a non-sense codon.

Preferably, the second part encodes the constant part of a human heavy chain, more preferably the constant part of the human γ4 chain. This second part may be a DNA fragment of genomic origin (comprising introns) or a cDNA fragment (without introns).

In another embodiment the DNA construct encodes a light chain or fragment thereof and comprises:
a) a first part which encodes a variable domain comprising alternatively framework and hypervariable regions; said hypervariable regions comprising in sequence DNA-CDR-L1-6A3 (SEQ ID NO: 17), DNA-CDR-L2-6A3 (SEQ ID NO: 18) and DNA-CDR-L3-6A3(SEQ ID NO: 19), this first part starting with a codon encoding the first amino acid of the variable domain and ending with a codon encoding the last amino acid of the variable domain, and
b) a second part encoding a light chain constant part or fragment thereof which starts with a codon encoding the first amino acid of the constant part of the light chain and ends with a codon encoding the last amino acid of the constant part or fragment thereof followed by a non-sense codon.

Preferably, the second part encodes the constant part of a human light chain, more preferably the constant part of the human κ chain.

The DNA constructs of the present invention may advantageously further comprise another part which is located upstream of the already described parts and which encodes a leader peptide; this additional part starting with the codon encoding the first amino acid and ending with the last amino acid of the leader peptide. This leader peptide is required for secretion of the chains by the host organism in which they are expressed and is subsequently removed by the host organism. Preferably, this part of the DNA construct encodes a leader peptide having an amino acid sequence substantially identical to the amino acid sequence of the heavy chain leader sequence as shown in SEQ ID NO: 20 (heavy chain of IgG1, starting with the amino acid at position −19 and ending with the amino acid at position −1), having an amino acid sequence as shown in SEQ ID NO: 22 (light chain of IgG1, starting with the amino acid at position −20 and ending with the amino acid at position −1), having an amino acid sequence substantially identical to the amino acid sequence of the heavy chain leader sequence as shown in SEQ ID NO: 30 (heavy chain of IgG4, starting with the amino acid at position −19 and ending with the amino acid at position −1), or, having an amino acid sequence as shown in SEQ ID NO: 31 (light chain of IgG4, starting with the amino acid at position −20 and ending with the amino acid at position −1).

Each of the DNA constructs are placed under the control of suitable control sequences, in particular under the control of a suitable promoter. Any kind of promoter may be used, provided that it is adapted to the host organism in which the DNA constructs will be transferred for expression. However, if expression is to take place in a mammalian cell, it is particularly preferred to use the promoter of an immunoglobulin gene.

The desired antibody may be produced in a cell culture or in a transgenic animal. A suitable transgenic animal may be obtained according to standard methods which include micro injecting into eggs the first and second DNA constructs placed under suitable control sequences transferring the so prepared eggs into appropriate pseudo-pregnant females and selecting a descendant expressing the desired antibody.

When the antibody chains have to be produced in a cell culture, the DNA constructs must first be inserted into either a single expression vector or into two separate but compatible expression vectors, the latter possibility being preferred.

Accordingly, the invention also provides an expression vector able to replicate in a prokaryotic or eukaryotic cell line which comprises at least one of the DNA constructs above described.

The present invention provides thus an expression vector comprising a polynucleotide of the present invention. The present invention also relates to an expression system, wherein said expression system or part thereof is capable of producing a polypeptide of the present invention, when said expression system or part thereof is present in a compatible host cell. An isolated host cell which comprises an expression system of the invention is also disclosed.

A method for producing a binding molecule, a polynucleotide, an expression vector, by means of recombinant DNA technology or by means of chemical synthesis is thus also envisaged in the present application.

Each expression vector containing a DNA construct is thus to be transferred into a suitable host organism. When the DNA constructs are separately inserted on two expression vectors, they may be transferred separately, i.e. one type of vector per cell, or co- transferred, this latter possibility being preferred. A suitable host organism may be a bacterium, a yeast or a mammalian cell line, this latter being preferred. More preferably, the mammalian cell line is of lymphoid origin e.g. a myeloma, hybridoma or a normal immortalized B-cell, but does not express any endogenous antibody heavy or light chain.

It is also preferred that the host organism contains a large number of copies of the vectors containing one or more DNA constructs per cell. If the host organism is a mammalian cell line, this desirable goal may be reached by amplifying the number of copies according to standard methods. Amplification methods usually consist of selecting for an increased resistance to a drug, said resistance being encoded by the expression vector.

In another aspect of the invention, there is provided a process for producing a multi-chain binding molecule of the invention, which comprises (i) culturing an organism which is transformed with at least one DNA construct of the invention and (ii) recovering an active binding molecule of the invention from the culture.

Alternatively, the heavy and light chains may for instance be separately recovered and reconstituted into an active binding molecule after in vitro refolding. Reconstitution methods are well-known in the art; Examples of methods are in particular provided in EP 120 674 or in EP 125 023.

Therefore a process may also comprise
(i) culturing a first organism which is transformed with a first DNA construct encoding a binding molecule of the invention and recovering a first binding molecule from the culture, and
(ii) culturing a second organism which is transformed with a second DNA construct encoding a binding molecule of the invention and recovering a second binding molecule from the culture, and
(iii) reconstituting in vitro an active binding molecule of the invention from the first binding molecule obtained in (i) and the second binding molecule obtained in (ii).

If needed, more organisms or cells, up to three, four, five, six, seven or eight, may be produced and used for providing more binding molecules.

In a similar manner, there is also provided a process for producing a single chain or single domain binding molecule of the invention which comprises (i) culturing an organism which is transformed with a DNA construct encoding a single chain or single domain binding molecule of the invention, respectively, and
(ii) recovering said molecule from the culture.

The NogoA and NiG binding molecules of the invention may exhibit very good nerve regeneration activity as shown, for example, in the granule cell neurite outgrowth model, as described below.

1. Granule Cell Neurite Outgrowth Assay (in vitro)

Brain tissue (cortex and brain stem) is taken and for each assay protein extract, is freshly prepared as described previously (Spillmann et al. 1998, Identification and characterization of a bovine neurite growth inhibitor (bNI-220), J Biol Chem. 1998 Jul. 24; 273(30):19283-93). Briefly, a piece of frozen tissue (e.g. 0.25g) is homogenized in 3-4 Vol of 60 mM Chaps -20 mM Tris pH 8.0-1 mM EDTA with a Protease blocker (10 µg/ml Aprotinin −5 µg/ml, Leupeptin −1 µg/ml Pepstatin −1 mM PMSF) at 4° C. The homogenate is put on a rotator at 4° C. for 30 min and centrifuged at 100'000 g for 45 min at 4° C. in a TLA 100.3 rotor (Beckman TL-100ultracentrifuge). From the supernatant, the protein concentration is determined using an absorption spectrophotometer.

Cerebellar granule cells are purified from trypsin digests of postnatal day 5-7 rat cerebellar tissue as described previously (Niederost et al 1999, Bovine CNS myelin contains neurite growth-inhibitory activity associated with chondroitin sulfate proteoglycans, J Neurosci. 1999 Oct. 15; 19(20):8979-89). The binding molecules of the invention are then pre-incubated for 30 min on the test substrate and removed before the cells are added. Cerebellar granule cells are added and incubated for 24 hours. To stop the experiment, 2 ml of 4% buffered formaldehyde is slowly added to the culture dishes. Monkey brain membrane protein extract prepared as described above was adsorbed overnight at 15 µg protein per cm2 culture dish on Greiner 4-well dishes (Greiner, Nuertingen, Germany). Dishes are washed three times with warm Hank's solution before plating the neurons. Postnatal day (5-7) rat cerebellar granule cells are prepared as described above and plated at 50,000 cells/cm2. Cells are cultured for 24 hr in serum-free medium, fixed, and immunostained with neurite marker MAB 1b (Chemicon monoclonal Ab, 1:200). For the staining of cell bodies DAPI (4',6-diamidino-2-phenyl-indole, dihydrochloride, from Molecular Probes) is used after staining with MAB1b. For antibody experiments, the anti-Nogo-A mAbs or control IgG Ab are preincubated on the dishes for 30 min and subsequently removed. Four fields at a defined distance to the edge of the well are randomly sampled for each well using a 40× objective by counting all intersections of neurites with a line placed through the center of the observation field. All cell bodies touching the line are also counted, and an index ratio of neurites per cell body is calculated for each well as reported previously (Simonen et al, 2003, Neuron 38,201-211). All counts are done blindly on coded experiments and expressed as an index of neurites per cell body. Results are expressed as mean index neurites/cell body.

Enhancement of neurite outgrowth of cerebellar granule cell in the non-permissive environment of the above prepared spinal cord extract by preincubation with a binding molecule of the invention may be observed.

The neutralizing activity of the molecules of the invention can also be estimated by measuring the regenerative sprouting and neurite outgrowth and functional recovery in the in vivo spinal cord injury models briefly described below.

2. Spinal Cord Injury Models in Rats and Monkeys (in vivo)

Adult Lewis rats are injured microsurgically by transecting the dorsal half of the spinal cord bilaterally at the level of the 8th thoracic vertebra. Laminectomy, anesthesia and surgery are described in Schnell and Schwab 1993 (Eur.J. Neurosci. 5: 1156-1171). Neuroanatomical tracing: The motor and sensory corticospinal tract is traced by injecting the anterograde tracer biotin dextran amine (BDA) into the cortex of the side opposite to the pump or the graft. BDA is transported to the spinal cord within 10-14 days and visualized using diaminobenzidine (DAB) as a substrate as described in Brösamle et al., (2000 J.Neurosci. 20: 8061-8068). Two weeks after a spinal cord injury destroying about 40% of the spinal cord segment T8, mainly in the dorsal half, including both main cervical spinal cord transections (CSTs): tracing of the CST in control animals show a moderate degree of reactive sprouting of the tract. This phenomenon corresponds to the spontaneous sprouting in response to injury well known in the literature. Injured rats being treated with the binding molecules of the invention or with pumps delivering the binding molecules of the invention may show an enhanced sprouting at the lesion site and regeneration of damaged axons neurite outgrowth of damaged neurites. Moreover the animals may show improved recovery of sensorimotor functions. Such functional tests are described previously (Merkler et al, 2001, J. Neuroscience 21,3665-73).

3. Tissue Distribution of Antibodies in Adult Monkey CNS

The binding molecules of the invention are purified as IgG and concentrated to 3 mg/ml in PBS. Mouse serum derived IgG (Chemicon Int., Temecula/Calif., USA) or a mAB directed against wheat auxin (AMS Biotechnology, Oxon/UK) are used as control treatments. Two male adult macaque monkeys (Macaca fascicularis) are used in this study for intrathecal infusion.

Surgical Procedures

Anaesthesia is induced by intramuscular injection of ketamine (Ketalar(r); Parke-Davis, 5 mg/kg, i.m.). Atropine is injected i.m. (0.05 mg/kg) to reduce bronchial secretions. An intravenous catheter is placed in the femoral vein for continuous perfusion with a mixture of propofol 1% (Fresenius (r)) and glucose 4% solution (1 volume of Propofol and 2 volumes of glucose solution), inducing a deeper anaesthesia. The animal is then placed in a stereotaxic framework. Under sterile conditions, a vertical midline skin incision is performed from C2 to Th1. The fascia cut and the spinal processes of C2 to Thi are exposed. The paravertebral muscles are retracted and the laminae of C6, C7 and Thi dissected. A complete C6 laminectomy and an upper C7 hemilaminectomy are then performed. The dura mater is exposed and incised longitudinally above the 7th and the 8th cervical spinal segments, corresponding to the rostral zone of the spinal portion covered by the 6th cervical lamina. A polyethylene tube (10 cm long), connected to an osmotic pump (Alzet(r), 2ML1; flow: 50 µg/hr) delivering the hNogo-A antibody, is inserted below the dura and pushed a few millimeters rostrally and attached to the dura with a suture. The osmotic pump is placed and secured in a cavity made in the mass of back muscles a few centimeter lower than the laminectomy, on the left side. The tube is secured along its trajectory with sutures to muscle tissue. The muscles and the skin are sutured and the animal recovered from anaesthesia usually 15-30 minutes after interruption of the venous perfusion with propofol. The animal is treated post-operatively with an antibiotic (Ampiciline 10%, 30 mg/kg, s.c.). Additional doses of Carprofen are given daily during one week.

The monkeys are sacrificed 8 days after implantation of the osmotic pump. Sedation is first induced with ketamine, as mentioned above, followed by a deep anaesthesia obtained by intraperitoneal (i.p.) injection of a lethal dose of pentobarbital (90 mg/kg). The animals are perfused transcardially with 0.4 litre of 0.9% saline, followed by 4 litres of fixative (4% solution of paraformaldehyde in 0.1 M phosphate buffer, pH=7.6). Perfusion is continued with 3 solutions of sucrose of increasing concentration (10% in fixative, 20 and 30% in phosphate buffer).

Histological procedures, immuno-fluorescence and -histochemistry

Brains and spinal cords of the monkeys are carefully dissected, cryo-protected in 30% sucrose and sectioned at 40 µm in a cryostate. For detection of infused mABs an anti-human secondary antibody is used (Jackson Laboratories). For double labelling, the following antibodies can be used: the rabbit AS472 (affinity purified) for endogenous Nogo-A (Chen, 2000), rabbit antibodies against GFAP for astrocytes, and a rabbit antibody against Cathepsin D (DAKO) for lysosomal localization. All the antisera are visualized by TRITC or FITC coupled corresponding secondary antibodies, or using the ABC-DAB system (Vector). Sections are analysed by epifluorescence on a Zeiss Axiophot or by confocal microscopy (ZEISS LSM 410).

The spinal cords are analysed at the infusion site and 6 cm caudal to it. High levels of the binding molecules of the invention are present at the infusion site. In the more caudal spinal cord, the central canal and cord surface are strongly labelled, whereas grey and white matter show a more homogenous labelling, which, however, is specific and clearly over background. A similar situation is present in the forebrain with strong labelling of surface and ventricles and good penetration of the Nogo-A antibody into the parenchyma.

These experiments show that spinal intrathecal infusion of antibodies against a CNS cell surface antigen lead to a good distribution of the binding molecules and antibodies of the invention through the CSF circulation in the inner (ventricles, central canal) and outer liquor spaces. The IgG antibodies penetrate well into the brain and spinal cord tissue. Whereas the negative control IgG antibody is washed out rapidly, the antibody against Nogo-A is retained in the brain and spinal cord tissue.

4. Tests for Nerve Repair and Functional Improvement in Spinal Lesions in monkeys Anaesthesia is induced by intramuscular injection of ketamine (Ketalar(r); Parke-Davis, 5 mg/kg, i.m.). Atropine is injected i.m. (0.05 mg/kg) to reduce bronchial secretions. An intravenous catheter is placed in the femoral vein for continuous perfusion with a mixture of propofol 1% (Fresenius (r)) and glucose 4% solution (1 volume of Propofol and 2 volumes of glucose solution), inducing a deeper anaesthesia. The animal is then placed in a stereotaxic framework. Under sterile conditions, a vertical midline skin incision is performed from C2 to Th1. The fascia cut and the spinal processes of C2 to Th1 are exposed. The paravertebral muscles are retracted and the laminae of C6, C7 and Th1 dissected. A complete C6 laminectomy and an upper C7 hemilaminectomy are then performed. In order to deliver the molecules in close proximity to the lesion, the free tip of a polyethylene tube attached to the pump is fixed under the dura a few millimeters rostrally to the lesion.

Behavioural manual dexterity tests can be performed according to the published procedure.

Manual dexterity is trained by placing the monkey seated in a primate chair in front of a Perspex modified "Brinkman board" (10 cm x 20 cm) containing 50 holes randomly distributed; 25 holes being oriented horizontally and 25 vertically {Liu, 1999 15428/id; Rouiller, 1998 13239 /id}. 2.7. The regeneration and sprouting of fibers can be assessed as described. The anterograde tracer injected in the right hemisphere is Biotinylated Dextran Amine (BDA, Molecular Probe(r), 10% in saline). In the left hemisphere, the fluorescent anterograde tracer Fluorescein Dextran (Molecular Probe(r), 10% in saline) is injected. Histological processing to visualise the tracers can be performed as described in details previously {Rouiller, 1994 8322/id}.

Therefore the invention also provides: (i) the use of the Nogo and NiG binding molecules of the invention in the nerve repair of a mammalian nervous system, in particular, a human nervous system, (ii) a method of repairing nerves of a mammalian nervous system, in particular, a human nervous system, which comprises administering an effective amount of the Nogo and NiG binding molecules of the invention to a patient in need of such treatment, or (iii) a pharmaceutical composition for nerve repair of a mammalian nervous system, in particular, a human nervous system, which comprises the binding molecules of the invention and a pharmaceutically acceptable carrier or diluent.

Therefore, the present invention provides a binding molecule, a polynucleotide, an expression vector or system, and a host cell according to the present invention for use as a medicament. In particular said binding molecule, polynucleotide, an expression vector or system or host cell may be used in the treatment of a disease of the peripheral (PNS) and/or central (CNS) nervous system or for the manufacture of a medicament for the treatment of a disease of the peripheral (PNS) and/or central (CNS) nervous system.

The present invention also provides a pharmaceutical composition comprising a binding molecule, a polynucleotide, an expression vector or system or a host cell according to the present invention in association with at least one pharmaceutically acceptable carrier or diluent. It also provides products containing said binding molecule, polynucleotide, expression vector or system or said host cell, or a pharmacologically acceptable derivative thereof, as a combined preparation for simultaneous, separate or sequentially use in the treatment of a disease of the peripheral (PNS) and/or central (CNS) nervous system.

A method of treatment of a disease of the peripheral (PNS) and/or central (CNS) nervous system comprising administering to a subject in need of such treatment an effective amount of a binding molecule, a polynucleotide, an expression vector or system or a host cell of the present invention is also envisaged.

The present invention further indicates in the examples that the pharmacological compositions and the products may be used for slow release of the binding molecule and/or for local deposition of the binding molecule at the site of injury.

As used herein, the term "slow release" or the equivalent terms "controlled release" or "extended release" refer to drug formulations that release an active drug, such as a polypeptide drug, including a NogoA or NiG binding molecule of the invention, such as an antibody directed to NogoA or NiG, over a period of time following administration to an individual. Extended release of polypeptide drugs, which can occur over a range of times, e.g., minutes, hours, days, weeks or longer, depending upon the drug formulation, is in contrast to standard formulations in which substantially the entire dosage unit is available for immediate absorbtion or immediate distribution via the bloodstream. Preferred extended release formulations result in a level of circulating drug from a single administration that is sustained, for example, for 8 hours or more, 12 hours or more, 24 hours or more, 36 hours or more, 48 hours or more, 60 hours or more, 72 hours or more 84 hours or more, 96 hours or more, or even, for example, for 1 week or 2 weeks or more, for example, 1 month or more. Extended release formulations are well described in the art and may be selected according to the preferred antibody release profile. Suitable polymers include biodegradable and non-biodegradable materials such as polylactic glycolic acid (PLGA).

As used herein, the term "epitope" refers to a unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a single variable domain in isolation.

As used herein, the term "neutralizing," when used in reference to a NogoA or NiG binding molecule as described herein, means that the binding molecule interferes with a measurable activity or function of NogoA or NiG. A NogoA or NiG binding molecule is a "neutralizing" polypeptide if it reduces a measurable activity or function of the target antigen, e.g. Nogo or NiG, by at least 50%, and preferably at least 60%, 70%, 80%, 90%, 95% or more, up to and including 100% inhibition. This reduction of a measurable activity or function of the target antigen can be assessed by one of skill in the art using standard methods of measuring one or more indicators of such activity or function. As an example, where the target is Nogo or NiG, neutralizing activity can be assessed using a Neurite growth assay described below.

In particular, the binding molecules of the invention are useful for axonal regeneration and improved sprouting after nerve fiber damage. Thus, the molecules of the invention have a wide utility in particular for human subjects. For example, the binding molecule of the invention are useful in the treatment of various diseases of the peripheral (PNS) and central (CNS) nervous system, i.e. more particularly in neurodegenerative diseases such as Alzheimer disease, Parkinson disease, Amyotrophic lateral sclerosis (ALS), Lewy like pathologies or other dementia in general, diseases following cranial, cerebral or spinal trauma, stroke or a demyeliating disease. Such demyelinating diseases include, but are not limited to, multiple sclerosis, monophasic demyelination, encephalomyelitis, multifocal leukoencephalopathy, panencephalitis, Marchiafava-Bignami disease, pontine myelmolysis, adrenoleukodystrophy, Pelizaeus-Merzbacher disease, Spongy degeneration, Alexander's disease, Canavan's disease, metachromatic leukodystrophy and Krabbe's disease. In one example, administration of the binding molecules of the invention can be used to treat a demyelinating disease associated with NogoA protein.

In another example, cells which express the binding molecules of the invention may be transplanted to a site spinal cord injury to facilitate axonal growth throughout the injured site. Such transplanted cells would provide a means for restoring spinal cord function following injury or trauma. Such cells could include olfactory ensheathing cells and stem cells of different lineages of fetal nerve or tissue grafts.

In addition, the Binding Molecules of the invention are useful for the treatment of degenerative ocular disorders which may directly or indirectly involve the degeneration of retinal or corneal cells including ischemic retinopathies in general, anterior ischemic optic neuropathy, all forms of optic neuritis, age-related macular degeneration, diabetic retinopathy, cystoid macular edema (CME), retinitis pigmentosa, Stargardt's disease, Best's vitelliform retinal degeneration, Leber's congenital amaurosis and other hereditary retinal degenerations, pathologic myopia, retinopathy of prematurity, and Leber's hereditary optic neuropathy, the after effects of corneal transplantation or of refractive corneal surgery, and herpes keratitis.

Furthermore, the Binding Molecules of the invention are useful for the treatment of psychiatric conditions, particularly schizophrenia and depression.

For these indications, the appropriate dosage will, of course, vary depending upon, for example, the particular molecule of the invention to be employed, the mode of administration and the nature and severity of the condition being treated. In general, the dosage preferably will be in the range of 1 μg/kg/day to 1 mg/kg/day.

The Binding Molecules of the invention are conveniently administered by pumps or injected as therapeutics at the lesioned site, e.g. they can be administered directly into the CNS intracranially or into the spine intrathecally to the lesioned site. The fluid filled space around the spinal cord is called the subarachnoid or intrathecal space. Cerebrospinal fluid (CSF) flows through this area, bathing and protecting the brain and spinal cord. An intrathecal drug pump may work much more efficiently than oral medication because it delivers medicine directly into the CSF, bypassing the path that oral medication takes through the body. Therefore in a preferred embodiment, the administration is done through intrathecal administration, e.g. using an externalized catheter connected to a portable pump. In a further preferred embodiment, intrathecal bolus injection is used. Suitable means and methods for intrathecal administration of drugs are those known in the art. Non-limiting examples of pumps are: the Alzet® pump and the Medtronic SynchroMed® or Isomed® infusion systems. The binding molecules can be infused continuously, or may preferably be administered as fixed doses at specific time intervals of 1, 2, 3, 4, 5, 6, 7, 10, 14, 21, or 30 days, for instance by direct bolus injections in the cerebrospinal fluid.

The Binding Molecules of the invention can be provided alone, or in combination, or in sequential combination with other agents. For example, the binding molecules of the invention can be administered in combination with anti-inflammatory agents such as but not limited to corticosteroids following stroke or spinal cord injury as a means for blocking further neuronal damage and inhibition of axonal regeneration, Neurotrophic factors such as Nerve growth factor (NGF), brain-derived neurotropic factor (BDNF) or other drugs for neurodegenerative diseases such as Exelon(tm) (Rivastigmine) or Levodopa (L-DOPA (3,4-dihydroxy-L-phenylalanine)). Other suitable combination partners for the treatment of stroke are Alteplase and Desmoteplase (DSPA, e.g. disclosed in WO90/09438). In one embodiment, the present invention provides a combination comprising a Binding Molecule of the invention and Desmoteplase, in particular for the treatment of stroke as well as pharmaceutical compositions comprising said combination. As used herein, two agents are said to be administered in combination when the two agents are administered simultaneously or are administered independently in a fashion such that the agents will act at the same time.

The structure of the active ingredients identified by code numbers, generic or trade names may be taken from the actual edition of the standard compendium "The Merck Index" or from databases, e.g. Patents International (e.g. IMS World Publications) or other databases provide by IMS Health. The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

Pharmaceutical compositions of the invention may be manufactured in conventional manner. E.g. a composition according to the invention comprising the molecules of the invention is preferably provided in lyophilized form. For immediate administration it is dissolved in a suitable aqueous carrier, for example sterile water for injection or sterile buffered physiological saline.

To aid in making up suitable compositions, the binding molecules of the invention and optionally a second drug enhancing the effect of the Binding Molecules of the invention, may be packaged separately within the same container, with instructions for mixing or concomitant administration. Optional second drug candidates are provided above.

The synergistic effect of a combination of the binding molecules of the invention and growth factors such as NGF may be demonstrated in vivo by the spinal cord injury models.

The present invention also relates to the use of the pharmaceutical composition of the invention for the preparation of slow release medicament of the binding molecule of the invention.

The present invention also relates to the use of the pharmaceutical composition of the invention for the preparation of a medicament for local deposition of the binding molecule of the invention at the site of injury.

The present invention further relates to the pharmaceutical of the invention for slow release of the binding molecule of the invention and for local deposition of the binding molecule of the invention at the site of injury.

The present invention also relates to a method for slow release of a binding molecule of the invention and for local deposition of a binding molecule of the invention.

The invention will be more fully understood by reference to the following examples. They should not, however, be construed as limiting the scope of the invention.

In the following examples all temperatures are in degree Celsius (° C.).

The monoclonal antibodies of attention in the Examples are Binding Molecules according to the present invention comprising the variable region of the light chain represented by SEQ ID NO: 5 and the variable region of the heavy chain represented by SEQ ID NO: 4 (6A3-IgG1), or comprising the variable region of the light chain represented by SEQ ID NO: 25 and the variable region of the heavy chain represented by SEQ ID NO: 24 (6A3-IgG4).

It is evident that in the paragraphs given above, the term "comprising" encompasses the term "consisting of".

The following abbreviations are used:
ELISA enzyme linked immuno-sorbant assay
FACS fluorescence activated cell sorting
FITC fluorescein isothiocyanate
FBS foetal bovine serum
FCS Fetal calf serum
HCMV human cytomegalovirus promoter
IgG immunoglobulin isotype G
mAb monoclonal antibody
VH variable region of the heavy chain
VL variable region of the light chain
LC light chain
HC heavy chain
CDR complementary determining region
BSA bovine serum albumin
aa amino acids
bp base pairs CNS central nervous system
HRP horse reddish peroxidase
RT room temperature
PBS phosphate-buffered saline
TBS Tris buffered saline
CEA carcinoembryonic antigen
IF immunofluorescence
IgG immunoglobulin G
PBS-T phosphate buffered saline with 0.05% Tween 20
PFA Paraformaldehyde

EXAMPLES

The invention is illustrated by the following non-limiting examples

Example 1

Sequence of the Medarex 6A3 Anti-hu-NogoA Monoclonal Antibody

A human IgG1 monoclonal antibody with high affinity for the human NIG-fragment of NogoA was selected. The original monoclonals were secreted from the mouse hybridoma cell clones which were derived by standard hybridoma technology using "Medarex mice"; recombinantly reconstituted mice with human immunoglobulin genes, by Medarex Inc., Annandale, N.J. The generation of Medarex Mice immunised with human NiG, and the production of hybridomas thereof, is well known in the art; conditions similar to these described in WO 2005/028508 have been followed. The antibody production level of most hybridoma's were very low; therefore recombinant DNA technology was employed to construct specialized expression vectors for high-level production of full antibody or the Fab-fragment in a cell line. The generation of purified Ab and Fab fragments of Abs is well known and described in detail in for instance WO 2005/028508. Similar steps have been followed for the generation of purified 6A3-mAb and 6A3-Fab. cDNAs encoding the variable regions of the heavy and the light chains of the 6A3-IgG1 antibody were amplified by PCR (polymerase chain reaction) from hybridoma mRNA, cloned and characterized by sequencing (FIGS. 1 and 2; SEQ ID NO 7 and 6).

Example 2

Fab and IgG4 Generation

The 6A3 mAb is of the IgG1 isotype. Human IgG1 isotype antibodies have a high affinity for cellular Fc receptors and can induce antibody-dependent cellular toxicity (AADC) and complement-dependent cytotoxicity (CDC) (Jerries et al., 2002, Hezareh et al., 2001). Moreover, IgG mAbs have been reported to rapidly efflux from the brain to the blood across the blood-brain barrier via Fc receptor-mediated reverse transcytosis (Zhang et al., 2001). In order to remove the potential Fc receptor-mediated interactions of the 6A3 IgG1 mAb, its isotype has been switched recombinantly to an IgG4 and also for recombinant production of a monovalent Fab fragment for high capacity expression in SP2/0 cells and *E. coli*.

The sequencing of the variable domains of the heavy and light chains of this human anti-Nogo-A antibody enabled the recombinant production of the 6A3-Fab fragment and the 6A3-IgG4 isotype antibody in high capacity producer cell lines.

For *E. coli* expression of the Fab fragment, both the cDNAs (SEQ ID NO:7 and SEQ ID NO:6) were cloned pASK116. The plasmid used to clone the cDNAs provides the constant domain genes of mouse IgG1/κ(Skerra, 1994). The two polypeptides chains of the antibody fragment are encoded on an operon under transcriptional control of the tetracyclin promoter. The first cistron codes for the heavy chain moiety of the Fab fragment. The VH domain was fused to the OmpA signal peptide at its N-terminus and to the CH1 domain of the murine class IgG1 at its C-terminal end. The second cistron encodes the light chain with the VL domain fused to the PhoA leader peptide and the murine CH1 domain. Upon induction of expression the two chains of the Fab fragment became simultaneously secreted into the periplasm of *E. coli* where the protein folding, disulfide bond formation and chain assembly occured. For expression of the Fab in *E. coli* the plasmids were transferred to BMP for large scale production.

For cloning of the light and heavy chain variable region of the 6A3 antibody for expression as an IgG4 antibody in SP2/0 cells, the corresponding cDNAs were cloned into the plasmid LCvec-AAL160 and hcMCPfin. For expression of the IgG4 full antibody, the plasmids were linearized with NotI for the LC construct and PvuI for the HC construct and transfected into SP2/0 cells.

6A3 IgG4 and 6A3 Fab monovalent fragment with his-tag have been successfully produced and purified. The recombinant antibodies exhibit high affinities for human NogoA fragment hNiG in BIAcore Experiments (see below). The respective Kd values being 0.14 nM and 1.1 nM confirming the correct and successful cloning and recombinant expression of the Ab retaining its high affinity for human NogoA fragment hNiG.

Coding regions and amino acids sequences of the heavy and the light chain of 6A3-Ig4 are shown in FIGS. 3 and 4 (SEQ ID NOs 24, 25, 28 and 28).

Example 3

Determination of the Complementarity Determining Regions of the 6A3-Ab

The complementarity determining regions of the variable heavy and light chain of the 6A3-antibody were determined using the Kabat database at the URL of www.bioinf.org.uk/abs/. The Kabat definition is based on sequence variability and is the most commonly used method to determine the CDRs of antibody variable regions (Wu T T, Kabat E A, 1970).

All 6 CDR-definitions correlated well with the experimentally determined amino acid sequences except for CDR-H2, where the typical residues before the CDR should be LEWIG, LEWVA was found (FIG. 5). However a number of variations are possible for CDR-H2.

Example 4

Biosensor Affinity Measurements for Mouse 6A3-IgG1, 6A3-IgG4 and 6A3 Fab to NiG

The affinity of the mouse 6A3-IgG1 mAb, 6A3-IgG4 mAb, and of the 6A3 Fab were measured by surface plasmon resonance (SPR) using a BIAcore 2000 optical biosensor (Biacore, Uppsala, Sweden) according to the manufacture's instructions. Recombinant human NIG was covalently immobilized on a flow cell of a CM5 sensor chip using amine-coupling chemistry. Briefly; the carboxymethlyladed dextran matrix was activated by injecting 35 µl of a solution containing 0.025M NHS and 0.1M EDC. For the immobilization on the sensor chip, the recombinant human NIG was diluted in 0.01M citrate buffer at pH 4 and injected at a flow rate of 5 µl/min to achieve coupling levels allowing affinity measurements. The deactivation of the remaining NHS-ester group was performed by injection of 35p1 of 1M ethanolamine hydrochloride (pH 8.5). The surface, of the sensor chip was regenerated by injecting 5 µl 0.1M HCl. For the measurement of the affinity, the antibodies were injected at different concentrations, ranging from 0.50 nM to 100 nM at a flow rate of 200 µl/min. After each injection, the sensor chip surface was regenerated with the injection of 10 µl 0.1M HCl without loss of binding activity on the surface. The kinetic constants, ka and kd and the affinity constants KA and KD were evaluated using the BIAevaluations 3.0 software supplied by the manufacturer.

Affinity measurement in BIAcore: The kinetic and the affinity binding constants of the mouse 6A3-IgG1 mAb, 6A3-IgG4 mAb, and of the 6A3 derived monovalent Fab fragment to recombinant human NogoA were measured in real time using surface plasmon resonance (SPR) technology (Biacore). For this analysis recombinant human NIG is coupled on a sensor chip surface and different concentrations of the antibodies are injected. Kinetic parameters of the binding interactions were derived from the sensograms by non-linear curve fitting. The affinity constants at equilibrium to human NIG for the antibodies were in the range of KDs 0.13nM to 2.5 nM for 6A3-IgG4, 6A3-IgG1, 6A3 Fab.

Example 5

Binding of anti-NogoA Antibodies NVP-6A3-Ab-NX-1 and NVP-IIC7-NX-1 to Endogenous Human NogoA In this example the binding of the antibodies to endogenous human Nogo-A is shown. To this end, two human cell lines which have been characterized previously to show oligodendritic-specific gene expression of Nogo-A, and subsequently for specific binding of the antibodies, were tested. The human oligodendroglial cell lines MO3.13 and HOG were used to characterize our two anti-Nogo-A antibodies NVP-6A3-Ab-NX-1 (6A3-Ab) and NVP-IIC7Ab-NX-1 (IIC7-Ab) with respect to their binding to endogenous Nogo-A. The cells can further be used to develop a bioassay for the characterization of the different antibody batches for clinical trials. In two independent experimental set-ups, the binding of 6A3-Ab to endogenous human Nogo-A in those cells were analysed and detected.

In a first step the MO3:13 cells were analyzed for the presence of Nogo-A mRNA by RT-PCR using primers specific for human Nogo-A. Secondly, the binding of both antibodies to endogenous Nogo-A was shown by immunprecipitation of MO3.13 cell lysates and immunodetection. Finally, specific immunofluorescent staining of the MO3.13 and HOG cells with the 6A3-Ab confirmed the results from the immunoprecipitations.

Thus, both 6A3-AB and 11C7-Ab were found to be capable of binding specifically to endogenous human Nogo-A.

Methods

Cell lines: The MO3.13 cells were obtained from Dr. N. Cashman, University of Toronto. They originated from the fusion of a 6-thioguanine-restistant mutant of the human rhabdomyosarcoma (RD) with adult human oligodendrocytes cultured from surgical specimen. The HOG cells were obtained from Dr. G. Dawson, University of Chicago. This cell line was established from a surgically removed oligodenroglioma. All cells were cultured in Dulbecco's Modified Eagle Medium with high glucose (Gibco) supplemented with Glutamax, 10% fetal calf serum and Penicillin/Streptomycin.

RT-PCR: Total RNA was prepared from 5×105 MO3.13 cells using Tripure reagent (Roche Diagnostics). After DNAse treatment, 1 µg of RNA was reverse transcribed in a total volume of 20 µl using Omniscript RT (Qiagen) and an oligo dT-primer. Primers used for PCR are specific for Nogo-A, amplifying a 194 by fragment starting at by position 1197 in full length human Nogo-A (5'-TGAGGGAAGTAGGGAT-GTGC-3' (SEQ ID NO: 32), 5'-CAGGTGATG-TACGCTCTGGA-3' (SEQ ID NO: 33)). A reaction was set up using 2 µl cDNA (or 0.1 µg RNA -RT), 5 µl 10× buffer, 3 µl dNTPs (5 mM each), 2.5 µl 5' Primer (10 µM), 2.5 µl 3' Primer (10 µM), 0.5 µl HotStar Taq-polymerase (Qiagen) and 34.5 µl H2O. The following PCR cycles were used: 95° C. 15 min., (94° C. 30 sec., 55° C. 30 sec., 72° C. 15 sec.)×35, 72° C. 10 min. –>4° C. After completion of the PCR, a 10 µl aliquot was analysed on a 2% ethidium bromide agarose gel.

Immunoprecipitation and Immunodetection: For each IP one 10 cm ø culture dish of MO3.13 cells grown to confluency was washed with PBS and the cells lysed, in 500 µl M-PER Mammalian Protein Extraction Reagent (Pierce) containing Complete protease inhibitor cocktail (Roche Diagnostics). The soluble fraction of the lysate was pre-cleaned with ProteinG-Sepharose (Sigma) for 15 minutes at RT (room temperature). To the pre-cleaned supernatant fresh ProteinG-Sepahrose and the corresponding antibody (50 nM final concentration) was added and incubated at 4° C. for 4 hours on a rotating shaker. Antibodies were either 6A3 IgG4, 11C7 IgG1 or anti-CEA IgG4 against a unrelated protein (carcinoembryonic antigen), which served as a negative control. An aliquot of each supernatant was kept for analysis of the unbound fraction; the Sepharose was washed 4 times with TNS buffer (10 mM TrisHCl pH 7.8, 1% (w/v) N-Laurylsarcosine, 100 mM NaCl), once with PBS, and the sepharose bound fraction was eluted with 20 µl SDS-PAGE loading buffer (Invitrogen). The samples were heated to 95oC for 5 minutes and a 10 µl aliquot each was run on a NuPage 4-12% gradient gel (Invitrogen) in MES-buffer.The proteins were blotted onto a cellulose membrane for 4 hours at 30 V and analysed for complete transfer with Ponceau staining. After transfer, the membrane was blocked over night at 4° C. in western blocking reagent (Roche Diagnostics) in PBS-T. For immunodetection, the membrane was incubated with the 6A3-IgG4 antibody at 1nM concentration for 2 hours at RT and subsequently with an anti-human peroxidase coupled secondary antibody for 1 hour at RT. Signals were detected using ECL-Advance (Amersham) and exposed to film for 1 minute.

Immunofluorescence: MO3.13 and HOG cells were plated in 8-well poly-D-lysine coated tissue chamber slides (Becton Dickinson) and grown until 80% confluent. After washing in PBS, the cells were fixed in 4% PFA for 30 min at room temperature. Nonspecific binding was blocked with 10% FCS, 0.1% Triton X-100 for 20 min. The cells were incubated in 1% FCS, 0.1% Triton X-100 for 1 hour with either 6A3-IgG4 5 nM or buffer only as negative control. After antibody incubation, the cells were washed 3 times with PBS and incubated with a Alexa Fluor 488 labeled anti human IgG antibody (Molecular Probes) at 1:200 dilution in PBS for 1 hour.

Results

RT-PCR: RT-PCR using the MO3.13 RNA as template resulted in a distinct DNA fragment of around 200 by (FIG. 6). No product was detected in the negative controls (RNA without reverse transcription and H2O). A PCR fragment was present at the expected size of 194 bps; no products were amplified in the negative control samples (DNAse treated RNA and H2O).

Figure 7:
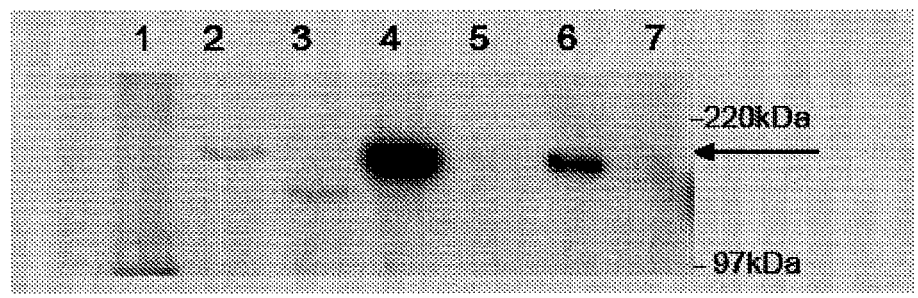
FIG. 7 Immunoblot detection of immunoprecipitated Nogo-A from MO3:13-cell lipids using 6A3 antibody. After immunoprecipitation (IP) of the MO3.13 cell-lysates and immunodetection with the 6A3 anti Nogo-A antibody a single strong band at the expected size (190kDa) was detected both for the 6A3-IgG4 (lane 4) and 11C7-IgG1 (lane 6) antibody.

Immunoprecipitation: After immunoprecipitation (IP) of the MO3.13 cell-lysates and immunodetection with the 6A3 anti Nogo-A antibody (FIG. 7) a single strong band at the expected size (190kDa) was detected both for the 6A3-IgG4 (lane 4) and 11C7-IgG1 (lane 6) antibody. No signal was detected after IP with the anti-CEA control antibody against a unrelated protein (carcinoembryonic antigen)(lane 1) and in the unbound fractions (lanes 5 and 7). A faint band is visible in the crude MO3.13 cell lysate before IP (lane 2). A faint nonspecific signal at a lower molecular weight is seen in the insoluble cell-lysate fraction (lane 3).

Immunofluorescence: Immunofluorescent staining of permeabilized MO3.13 cells and HOG cells with the 6A3-IgG4 and the Alexa-Fluor 488-labeled anti human secondary antibody resulted in very bright staining of the cells (FIGS. 8a and 8b, left part), whereas virtually no signal was detected with the secondary antibody only (right part).

Discussion

RT-PCR analysis of the MO3.13 cells using Nogo-A specific primers for PCR resulted in a DNA fragment of expected size (194 bp), whereas no PCR product was detected with the nonreverse transcribed RNA sample or the water control. From this result we conclude that the cells express endogenous Nogo-A.

Immunoprecipitation from MO3.13 cell lysates and immunodetection with the anti-Nogo-A antibody 6A3 showed a single strong Nogo-A band at the expected size (190kDa). In contrast, the anti-CEA (IgG4) control antibody did not yield a band of corresponding size. The difference in intensity between the bands resulting from the 6A3 and 11C7 immunoprecipitations are most likely due to the different affinities of the different antibody isotypes to Protein G Sepharose (affinity 6A3 >affinity 11C7). The results from the intracellular immunofluorescent staining of both the MO3.13 and the HOG cells showed that the 6A3-IgG4 binds to endogenous Nogo-A.

From these results it was concluded that the two cell lines endogenously express Nogo-A and that both the 6A3 IgG4 (6A3-Ab) and the 11C7 IgG1 (11C7-Ab) antibody bind specifically to endogenous human Nogo-A. These findings suggest that the MO3.13 cell line may be used to establish Nogo-A binding assays for, for instance, antibody characterization.

Example 6

Effect of 6A3 Treatment on the Functional Recovery of Macaque Monkeys Subjected to Brain Lesions In a further study, macaque monkeys were subjected to a lesion as described previously and treated with a 4 week intrathecal infusion of 6A3 or control IgG from the time of lesion. Manual dexterity for the affected left hand was determined using the modified Brinkmann board test under conditions as described herein before. 6A3 treatment improved the rate and degree of functional recovery compared to control IgG treatment. When the size of the lesion was determined at the end of the experiment, functional recovery of control IgG treated monkeys was found to roughly inversely correlate with lesion size, varying from 90% for a 50% lesion to 53% for a 90% lesion. Conversely, the amount of recovery in the anti-Nogo-A mAb treated animals was not significantly affected by lesion size and for 6A3 treated animals almost reached their pre-lesion performance even when the lesion size was as high as 85%.

Example 7

CSF Retention and Half life of the 6A3 Antibody in Human Subjects

Figure 9:
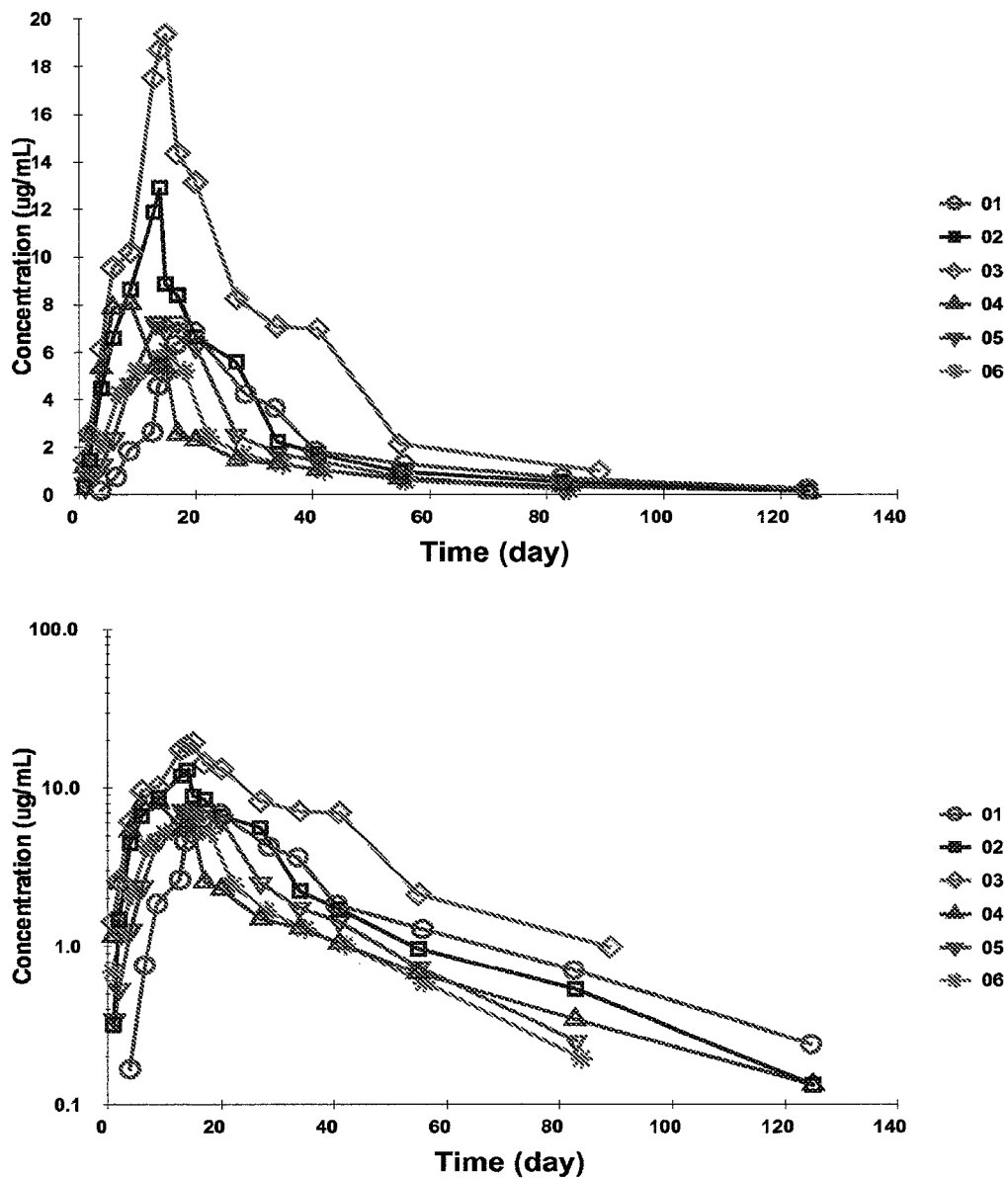
FIG. 9 Serum concentrations 6A3 antibody measured in 6 subjects up to two months.
Figure 10:
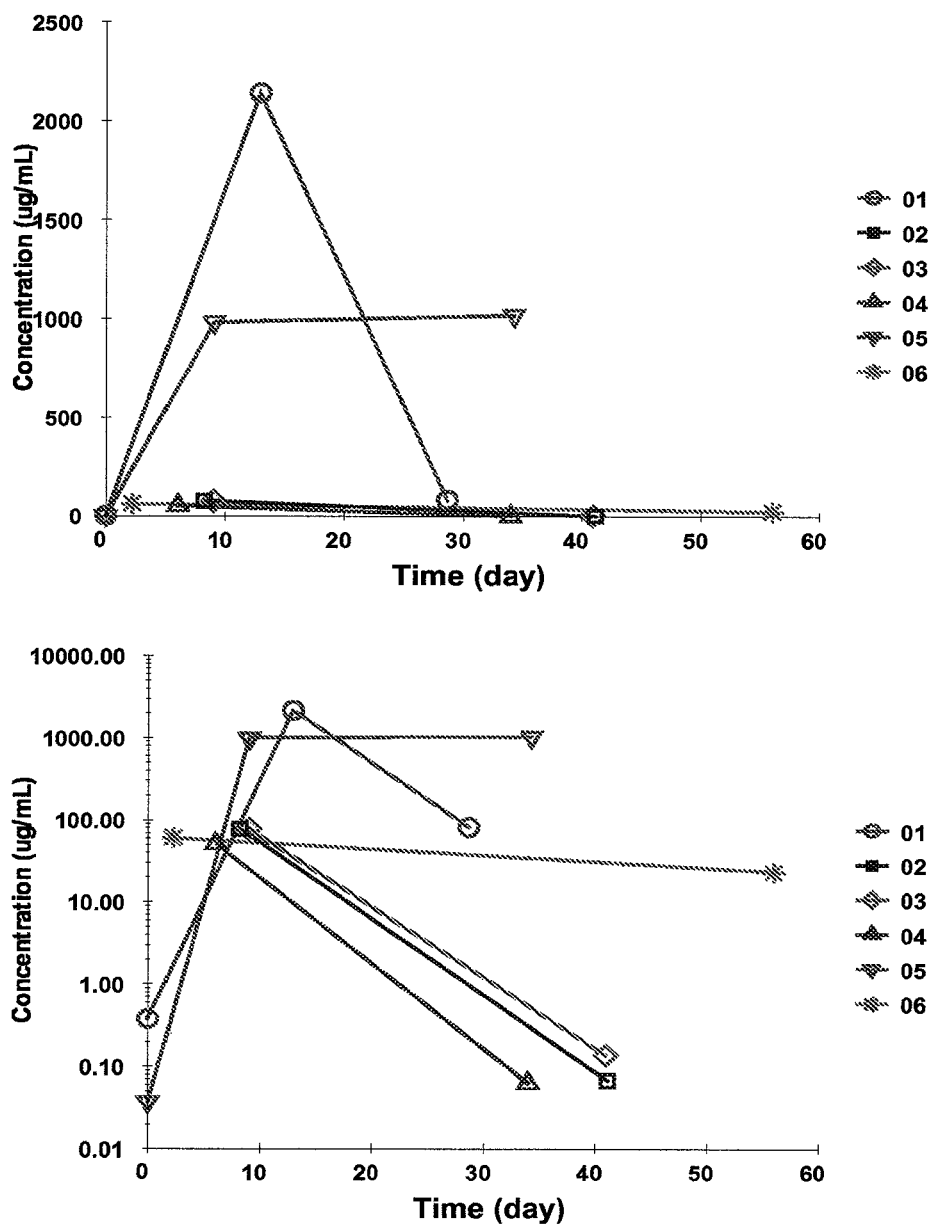
FIG. 10 CSF concentrations 6A3 antibody measured in 6 subjects up to two months

The CSF retention and half life of the 6A3 antibody in human subjects were determined after CSF infusions during 14 days (daily dose 15 mg/day) and individual concentrations measured in serum and CSF (FIGS. 9 and 10). The CSF concentrations remained constant or declined only marginally, in two cases lasted to Days 34 and 56, i.e. approximately 20 and 42 days after the end of the infusion, as compared to the levels measured during the infusion, which indicates the surprisingly long residency and/or half life in the CSF of 6A3. This pharmacokinetic behaviour would enable different administration routes and dosis regimens with longer intervals. Bolus injections into the CSF during intervals of 2 or more days or weeks would be feasible. The 6A3 antibody would also be suitable for controlled release formulations, such as formulation in biodegradable or non-biodegradable polymers and implants.

Example 8

Figure 11:
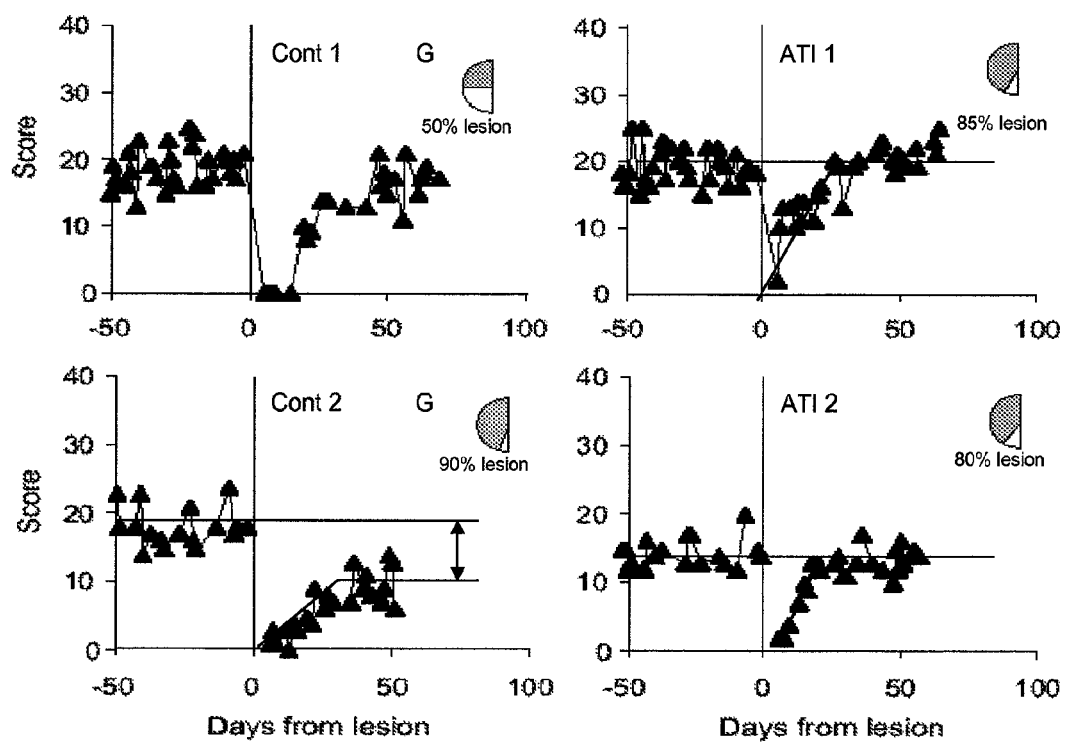

Efficacy in Macaque SCI Model 3 monkeys are subjected to a unilateral section of the spinal cord at the C7/C8 border, an injury known to disable the generation of precise fine finger movements, and implanted with an osmotic Alzet® pump which intrathecally delivers to the lesion site either mouse IgG antibody in the control animal or 6A3 antibody in the treated animals for 4 weeks at a dose of 1 mg/day (FIG. 11 and Freund et al., Nat Med 12:7 90-2, 2006). Manual dexterity is assessed by food pellet retrieval from vertical and horizontal slots in a modified Brinkman board test. Other behavioral tasks include food pellet retrieval from a drawer, ballistic arm movements, foot motor capacity for grasping food and behavioral observation on pain and discomfort. The tests are performed from 60 days prior to the lesion to 120 days after the lesion at regular intervals.

Monkeys were subjected to a unilateral spinal cord section and treated intrathecally with either mouse IgG control antibody (n=2, i.e. Cont. 1 with 50% lesion and Cont. 2 with 90% lesion) or 6A3 (n=2, i.e. ATI1 with 85% lesion and ATI2 with 80% lesion) at a dose of 1 mg/day for 4 weeks (monkey weights: Cont 1, 5.1 kg, Cont 2, 4.1 kg, ATI 1, 5.0 kg, ATI 2, 4.5 kg). Results are shown as total number of pellets during test sessions on specific trial days. Values were calculated using individual behavioral scores pre-lesion and post-lesion when the level of performance remained stable. 6A3 antibody treatment in the monkeys gave a gradual improvement in food pellet retrieval using the affected left hand from horizontal and vertical slots in comparison to a control IgG treated monkey. The control monkey showed a total persistent deficit in retrieving pellets from the horizontal slots, a movement which requires greater manual dexterity than retrieval from vertical slots.

After recovery had reached a maximal level in the Brinkmann board test, the monkeys were tested for their capacity to grab the handle of a drawer with their affected left hand, to pull it open and extract a food pellet from a well in the drawer. The control IgG treated monkey with a lesion of 90% (Cont. 2) was totally unable to grab the handle and to open the drawer. The arm movement was slower than normal and the hand shaping abnormal. This can be derived from the double arrowed line, indicating a clear difference between the activity before the lesion and the activity after the lesion and treatment with control IgG antibody, indicating only partial recovery. 6A3 antibody treated animals with 85% (ATI-1) or 80% (ATI-2) lesions recovered the capacity to perform the task both rapidly and effectively, irrespective of lesion size. There is no substantial difference in activity before and after the lesion when treated with the 6A3 antibody, pointing to a complete recovery due to the 6A3 antibody treatment. The 6A3 antibody treatment thus provides a clear beneficial effect on recovery after induced brain lesions in Macaque, as compared to the IgG control antibody treatment.

Example 9

Clinical Trials

A suitable clinical study is described as follows:

The study has three phases: Screening Phase (including Baseline), open-label Treatment Phase and at least a 22-week Follow-up Phase. The study is conducted under the supervision of an independent Data Safety Monitoring Board (DSMB).

A total of 22 patients are enrolled in 4 partially overlapping, sequential cohorts to receive a continuous infusion of 6A3 antibody. All patients have a follow-up period for at least 22 weeks post infusion for further safety evaluation.

Patient allocation and treatment dose and duration by cohort is as follows:
  Cohort 1: 3 paraplegic patients receive 5 mg [in 2.5 ml] over 24h;
  Cohort 2: 3 paraplegic patients receive 30 mg [in 2.5 ml] over 24 h;
  Cohort 3: 6 paraplegic patients receive up to 30 mg/day [in 2.5 ml/day] over 14 days.
  Cohort 4: 10 para- and tetraplegic patients receive up to 30 mg/day [in 2.5 ml/day] over 28 days.

Patients are closely monitored for a period of at least six months following start of infusion. The status of the patients is closely monitored by vital signs measurements, ECG recordings (interpretation by a central facility) and laboratory evaluations based on matrices blood, urine and CSF. Neurological examinations using the ASIA scale (Applicable Standard Neurological Classification of Spinal Cord Injury by the American Spinal Injury Association) (Ditunno, et al, 1994; American Spinal Cord Injury Association. Paraplegia 32(2): 7080.) is performed by qualified clinicians to assess efficacy, but also to assess potential exacerbation of the spinal cord injury. A total of four cerebral and spinal MRIs is performed for each patient. CSF samples are taken at three timepoints from each patient (pre-dose, during the treatment phase and during the follow-up phase) for pharmacokinetic (PK) analysis. Blood samples are also obtained for PK analysis through the treatment and follow-up phases. Data from all the patients are reviewed by the independent DSMB as per protocol.

The invention claimed is:

1. A method of treatment of a disease of the peripheral (PNS) and/or central (CNS) nervous system comprising administering to a subject in need of such treatment an effective amount of an isolated protein comprising at least one antigen binding site which specifically binds to the human NogoA polypeptide (SEQ ID NO: 2) or human NiG (SEQ ID NO: 3), said antigen binding site comprising:

in sequence the hypervariable regions CDR-H1, CDR-H2, and CDR-H3, wherein the hypervariable regions are CDR-H1-6A3 (SEQ ID NO: 8), CDR-H2-6A3 (SEQ ID NO: 9) and CDR-H3-6A3 (SEQ ID NO: 10), respectively; and in sequence the hypervariable regions CDR-L1, CDR-L2, and CDR-L3, wherein the hypervariable regions are CDR-L1-6A3 (SEQ ID NO: 11), CDR-L2-6A3 (SEQ ID NO: 12) and CDR-L3-6A3 (SEQ ID NO: 13), respectively.

2. The method according to claim 1, wherein the disease is a neurodegenerative disease chosen from the group consisting of Alzheimer disease, Parkinson disease, Amyotrophic lateral sclerosis (ALS), traumatic brain injury, spinal cord injury, stroke and a demyelinating disease.

3. The method according to claim 1, wherein the administration is performed locally at the site of an injury, intracranially or intrathecally.

* * * * *